(12) United States Patent
Lecellier et al.

(10) Patent No.: US 9,175,334 B2
(45) Date of Patent: Nov. 3, 2015

(54) IDENTIFYING VIRAL CELL TROPISM

(75) Inventors: Charles-Henri Lecellier, Les Cres (FR);
Valerie Courgnaud, Montpellier (FR);
Manuella Bouttier, Montpellier (FR);
Diane Descamps, Paris (FR); Gilles Collin, Poissy (FR)

(73) Assignees: CENTRE NATIONAL DE LA RECHERCHE SCIENTIFIQUE, Paris (FR); ASSISTANCE PUBLIQUE-HOPITAUX DE PARIS, Paris (FR); UNIVERSITE MONTPELLIER 2 SCIENCES ET TECHNIQUES, Montpellier (FR); UNIVERSITE PARIS-DIDEROT-PARIS 7, Paris (FR)

( * ) Notice: Subject to any disclaimer, the term of this patent is extended or adjusted under 35 U.S.C. 154(b) by 488 days.

(21) Appl. No.: 13/394,002

(22) PCT Filed: Sep. 1, 2010

(86) PCT No.: PCT/FR2010/051817
§ 371 (c)(1),
(2), (4) Date: Oct. 19, 2012

(87) PCT Pub. No.: WO2011/027075
PCT Pub. Date: Mar. 10, 2011

(65) Prior Publication Data
US 2013/0040832 A1 Feb. 14, 2013

(30) Foreign Application Priority Data
Sep. 4, 2009 (FR) .................................. 09 56045

(51) Int. Cl.
*C12Q 1/68* (2006.01)
*C12Q 1/70* (2006.01)

(52) U.S. Cl.
CPC .................................. *C12Q 1/6813* (2013.01)

(58) Field of Classification Search
None
See application file for complete search history.

(56) References Cited

U.S. PATENT DOCUMENTS 7,393,634 B1 * 7/2008 Ahuja et al. ...................... 435/5

FOREIGN PATENT DOCUMENTS

WO    WO 2009/033185    3/2009

OTHER PUBLICATIONS

Van Baelen et al ("HIV-1 coreceptor usage determination in clinical isolates using clonal and population-based genotypic and phenotypic assays", J Virol Methods, Available online Jul. 19, 2007: pp. 61-73).*
Abstract of Van Baelen et al., "HIV-1 coreceptor usage determination in clinical isolates using clonal and population-based genotypic and phenotypic assays", J. Virol Methods, vol. 146 (1-2), pp. 61-73 (2007).
English translation of the International Search Report mailed in connection with International Application No. PCT/FR2010/051817 on Jan. 31, 2011.

* cited by examiner

*Primary Examiner* — Catherine S Hibbert
(74) *Attorney, Agent, or Firm* — Davidson, Davidson & Kappel LLC

(57) ABSTRACT

The invention relates to an in vitro method for identifying microRNAs or the target mRNAs thereof, the expression of which during the infection of cells by a virus using a cell receptor and at least one cell co-receptor for entering the cell, is specifically modified on the basis of the cell co-receptor used by the virus for its entering the cells, comprising:
  i) determining the microRNA expression levels in a test cell expressing a receptor, a first co-receptor and at least one other co-receptor, after infection by a first virus using the first co-receptor and by at least one other virus using another co-receptor, respectively;
  ii) identifying the microRNAs, the expression level of which is modulated during the infection by each of the viruses in relation to the expression level in the uninfected cells;
  iii) comparing the thus-identified microRNAs;
  iv) selecting the microRNAs, the modification of the expression level of which is specific to the use of a co-receptor;
  v) optionally identifying the target mRNAs of the thus-selected microRNAs.

6 Claims, 1 Drawing Sheet

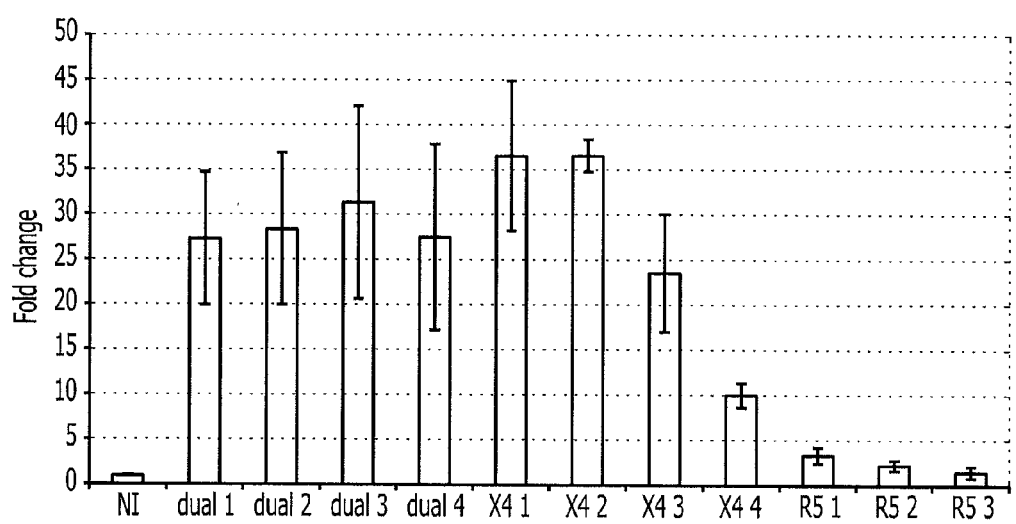

IDENTIFYING VIRAL CELL TROPISM

This application is a national phase application under 35 U.S.C. §371 of International Application No. PCT/FR2010/051817 filed on Sep. 1, 2010, which claims priority to French Application No. 0956045, filed on Sep. 4, 2009, the disclosures of which are all hereby incorporated by reference herein.

FIELD OF THE INVENTION

The present invention relates to a method for characterizing cell tropism of a virus, notably of the Human Immunodeficiency Virus (HIV), and in particular the HIV virus capacity of using CXCR4 and CCR5 receptors in order to enter the cells.

TECHNICAL BACKGROUND

Entry of the HIV virus in cells involves several viral proteins including the envelope proteins gp41 and gp120. The first step of the replication cycle of the HIV virus involves the binding of the virus to auxiliary T4 lymphocytes by interaction of the gp120 protein with the CD4 cell protein. Further, in order that the fusion of the viral and cell membranes occurs, the HIV virus has to interact with a cell co-receptor. The most important co-receptors in vivo are the receptors of chemokines CXCR4 and CCR5. The use of the different co-receptors is associated with the time-dependent change in the immune deficiency and therefore to the infection: at the beginning of the infection, so-called R5 viruses interact with the CCR5 co-receptor and then at a later stage, certain viruses (so-called X4 viruses) use the CXCR4 co-receptor. At this stage, the viral population either comprises a mixture of R5 and X4 viruses, or viruses with double R5/X4 tropism. In certain cases, the viruses R5 may directly induce the occurrence of AIDS, however it is the occurrence of X4 viruses which is generally associated with the development of the disease. It is therefore essential to be able to detect early the occurrence of X4 viruses in the patient.

Thus, a certain number of methods having the purpose of determining cell tropism of HIV viruses have been developed.

For example, the TROFILE test (MONOGRAM) is a phenotype test of the HIV virus proposed by Monogram Biosciences and Pfizer. First of all, a library of vectors containing the regions coding for the envelope of HIV viruses of a patient is elaborated. These vectors are then amplified and the regions coding for the envelope are cloned in a vector expressing a HIV virus without any envelope protein and expressing the gene of luciferase. Finally, the recombinant viruses obtained from these vectors are used for infecting cells expressing CD4 and CCR5 or CXCR4. The virus capacity of infecting these cells is determined by measuring the light emission produced by luciferase. This test has several drawbacks, as notified in November 2007 by the TRT-5 to the Afssaps (French Agency for the Safety of Health Products) and the HAS (<<Haute Autorité de la Santé>>, French National Authority for Health). First of all it has a very high cost. Further, the time for receiving the results is from four to five weeks, which is not compatible with fast decision-making in the case of a change of treatment. Further, it is not impossible that a change in viral tropism may occur in certain patients within such a time. Moreover, no profile test is available for viruses of the HIV-2 types.

Therefore, there exists a real need for simple, fast, reliable and inexpensive alternative tests allowing determination of the cell tropism of HIV viruses. The object of the present invention is to provide such tests.

SUMMARY OF THE INVENTION

The present invention results from the unexpected discovery by the inventors that the expression of miRNA in a cell which may be infected by a HIV virus is modulated depending on the co-receptor used by the HIV virus for entering the cell.

Thus, the present invention relates to an in vitro method for identifying microRNAs or their target mRNAs, the expression of which, during the infection of cells by a virus using a cell receptor and at least one cell co-receptor for entering the cell, is specifically modified according to the cell co-receptor used by the virus for its entry into the cells, comprising:

i) determining the expression levels of microRNA in a test cell, expressing a receptor, a first co-receptor and at least one other co-receptor, after infection by a first virus using the first co-receptor and by at least one other virus using another co-receptor, respectively;
  ii) identifying the microRNAs for which the expression level is modulated during the infection by each of the viruses relatively to the expression level in uninfected cells;
  iii) comparing the thus-identified microRNAs;
  iv) selecting the microRNAs for which the modification of the expression level is specific to the use of a co-receptor;
  v) optionally identifying the target mRNAs of the thus-selected microRNAs.

The invention also relates to an in vitro method for identifying a cell co-receptor used by a virus using a cell receptor and at least one cell co-receptor for entering a cell, in a patient infected by the virus, comprising:

i) putting a sample from the patient which may contain the virus in contact with a test cell expressing a cell receptor of the virus and at least one cell co-receptor of the virus;
  ii) determining the expression level of at least one miRNA and/or at least one target mRNA of a miRNA in the test cell;
  iii) comparing the expression level with a predetermined value;
  iv) inferring therefrom whether the virus uses a cell co-receptor expressed by the test cell, or not.

DESCRIPTION OF THE INVENTION

The term of <<miRNA>> or <<microRNA>> refers to a class of RNAs generally from 20 to 25 nucleotides long, involved in post-transcriptional regulation of certain specific genes by degrading or blocking the translation of the mRNA stemming from the transcription of these genes. By <<target mRNA>> of an miRNA, is meant an mRNA for which it is known or for which it is determined that it is degraded or for which the translation is blocked by said miRNA. miRNAs are notably described in Griffiths-Jones ((2004) *Nucleic Acids Res.* 32:D109-D111), in Griffiths-Jones et al. ((2008) *Nucleic Acids Res* 36:D154-D158) and in the database on miRNAs (miRBase, http://microRNA.sanger.ac.uk).

The expression <<virus>> as used herein comprises all the types of viruses. In particular, the virus may be selected from the group of viruses whose variants or species are more or less pathogenic, for example retroviruses in particular the HIV virus, influenza viruses, corona viruses, viruses of measles, herpes viruses (including the EBV, Simplex and CMV viruses), papilloma viruses. Preferentially, the virus is a retrovirus selected from human retroviruses notably HIV, HTLV-1 and XMRV. Still more preferentially, the virus is the HIV and in particular the HIV-1 and HIV-2 viruses (notably described in the HIV databases, http://www.hiv.lanl.gov/content/index). If the virus according to the invention is the HIV, the viruses used for carrying out infections may for example be prototype viruses such as HIV-1, NL4.3, HIV-2 ROD or HIV-1 NLAD8 viruses or viruses from a patient. The HIV viruses according to the invention may use one or more co-receptors for entering the target cells. Preferentially, in the methods for identifying micro-RNA according to the invention, the HIV viruses used only use a single type of co-receptor for entering a cell.

The term <<patient>> designates a human being, infected by a virus. Preferentially, the virus is the HIV. The patient may then possibly have developed AIDS (Acquired Immuno-Deficiency Syndrome). Possibly, the patient is under anti-retroviral treatment, for example under a HAART (highly active anti-retroviral therapy) treatment.

The terms <<receptor>> and <<cell receptor>> according to the invention designate a cell surface structure, generally a protein, involved in the recognition of a target cell by a virus and generally resulting in the binding of this virus to the target cell. The terms <<co-receptor>> and <<cell co-receptor>> gather all of the cell surface proteins participating in the entry of the virus, the cell receptor being excluded.

When the virus is the HIV, the terms <<co-receptor>> and <<cell co-receptor>> more specifically gather all of the cell surface proteins participating in the entry of the virus in addition to the interaction between the virus and the cell receptor CD4. The entry of an HIV virus in a host cell involves the fusion between the cell and viral membranes. In particular, the co-receptor may be selected from the group consisting of CXCR4, CCR5, CCR3, CCR2, CCR1, CCR4, CCR8, CCR9, CXCR2, STRL33, V28, gpr1, gpr15 and ChemR23. Preferentially, the co-receptor is CCR5 or CXCR4.

CXCR4 is also known under the names of Fusin, LESTR and NPY3R. The CRCR4 gene here designates preferentially the sequence of the human CXCR4 gene whose mRNA sequence may, for example, be SEQ ID NO: 1 or any allelic or polymorphic variant thereof as well as the ortholog sequences present in other species. The gene CXCR4 codes for the CXCR4 protein which may have the sequence represented by SEQ ID NO: 2 or any natural variant thereof.

CCR5 is also known under the names of CKR-5 and CMKRB5. The gene CCR5 preferentially designates here the sequence of the human CCR5 gene whose mRNA sequence may, for example, be SEQ ID NO: 3 or any allelic or polymorphic variant thereof as well as the ortholog sequences present in other species. The CCR5 gene codes for the CCR5 protein which may have the sequence represented by SEQ ID NO: 4 or any natural variant thereof.

CCR3 is also known under the names of CC-CKR-3, CKR-3 and CMKBR3. The CCR3 gene preferentially designates here the sequence of the human CCR3 gene whose mRNA sequence may, for example, be SEQ ID NO: 5 or any allelic or polymorphic variant thereof as well as the ortholog sequences present in other species. The CCR3 gene codes for the CCR3 protein which may have the sequence represented by SEQ ID NO: 6 or any natural variant thereof.

CCR2 is also known under the names of CCR2b and CMKBR2. The CCR2 gene preferentially designates here the sequence of the human CCR2 gene whose mRNA sequence may, for example, be SEQ ID NO: 7 or any allelic or polymorphic variant thereof as well as the ortholog sequences present in other species. The CCR2 gene codes for the CCR2 protein which may have the sequence represented by SEQ ID NO: 8 or any natural variant thereof.

CCR1 is also known under the names of CKR1 and CMKBR1. The CCR1 gene preferentially designates here the sequence of the human CCR1 gene whose mRNA sequence may, for example, be SEQ ID NO: 9 or any allelic or polymorphic variant thereof as well as the ortholog sequences present in other species. The CCR1 gene codes for the CCR1 protein which may have the sequence represented by SEQ ID NO: 10 or any natural variant thereof.

CCR4 is also known under the name of CKR-4. The CCR4 gene preferentially designates here the sequence of the CCR4 gene whose mRNA sequence may, for example, be SEQ ID NO: 11 or any allelic or polymorphic variant thereof as well as the ortholog sequences present in other species. The CCR4 gene codes for the CCR4 protein which may be of a sequence represented by SEQ ID NO: 12 or any natural variant thereof.

CCR8 is also known under the names of ChemR1, TER1 and CMKBR8. The CCR8 gene preferentially designates here the sequence of the human CCR8 gene whose mRNA sequence may, for example, be SEQ ID NO: 13 or any allelic or polymorphic variant thereof as well as the ortholog sequences present in other species. The CCR8 gene codes for the CCR8 protein which may have the sequence represented by SEQ ID NO: 14 or any natural variant thereof.

CCR9 is also known under the name of D6. The CCR9 gene preferentially designates here the sequence of the human CCR9 gene whose mRNA sequence may, for example, e be SEQ ID NO: 15 or any allelic or polymorphic variant thereof as well as the ortholog sequences present in other species. The CCR9 gene codes for the CCR9 protein which may have the sequence represented by SEQ ID NO: 16 or any natural variant thereof.

CXCR2 is also known under the name of IL-8RB. The CXCR2 gene preferentially designates here the sequence of the human CXCR2 gene whose mRNA sequence may, for example, be SEQ ID NO: 17 or any allelic or polymorphic variant thereof as well as the ortholog sequences present in other species. The CXCR2 gene codes for the CXCR2 protein which may have the sequence represented by SEQ ID NO: 18 or any natural variant thereof.

STRL33 is also known under the names of Bonzo, CXCR6 and TYMSTR. The STRL33 gene preferentially designates here the sequence of the human STRL33 gene whose mRNA sequence may, for example, be SEQ ID NO: 19 or any allelic or polymorphic variant thereof as well as the ortholog sequences present in other species. The STRL33 gene codes for the STRL33 protein which may have the sequence represented by SEQ ID NO: 20 or any natural variant thereof.

V28 is also known under the names of CMKBRL1, CX3CR1 and GPR13. The V28 gene preferentially designates here the sequence of the human V28 gene whose mRNA sequence may, for example, be SEQ ID NO: 21 or any allelic or polymorphic variant thereof as well as the ortholog sequences present in other species. The V28 gene codes for the V28 protein which may have the sequence represented by SEQ ID NO: 22 or any natural variant thereof.

The gpr1 or GPR1 gene preferentially designates here the sequence of the human gpr1 gene whose mRNA sequence may, for example, be SEQ ID NO: 23 or any allelic or polymorphic variant thereof as well as the ortholog sequences present in other species. The gpr1 gene codes for the gpr1 protein which may have the sequence represented by SEQ ID NO: 24 or any natural variant thereof.

gpr15 or GPR15 is also known under the name of BOB. The gpr15 gene preferentially designates here the sequence of the human gpr15 gene whose mRNA sequence may, for example, be SEQ ID NO: 25 or any allelic or polymorphic variant thereof as well as the ortholog sequences present in other species. The gpr15 gene codes for the gpr15 protein which may have the sequence represented by SEQ ID NO: 26 or any natural variant thereof.

Apj is also known under the names of angiotensin-receptor-like, apelin receptor (APLNR) and AGTRL1. The Apj gene preferentially designates here the sequence of the human Apj gene whose mRNA sequence may, for example, be SEQ ID NO: 27 or any allelic or polymorphic variant thereof as well as the ortholog sequences present in other species. The Apj gene codes for the Apj protein which may have the sequence represented by SEQ ID NO: 28 or any natural variant thereof.

The ChemR23 gene is also known under the names of CMKLR1 and DEZ. The ChemR23 gene preferentially designates here the sequence of the human ChemR23 gene whose mRNA sequence may, for example, be SEQ ID NO: 29 or any allelic or polymorphic variant thereof as well as the ortholog sequences present in other species. The ChemR23 gene codes for the protein ChemR23 protein which may have the sequence represented by SEQ ID NO: 30 or any natural variant thereof.

According to the invention, by <<test cell>> is meant any cell which may be infected by a virus according to the invention. Preferentially, when the virus is the HIV, the test cell according to the invention expresses CD4, a first and at least one other co-receptor of the HIV virus as defined above. Still preferentially, the test cell according to the invention expresses CXCR4 and CCR5. A test cell according to the invention may naturally express these receptors or be genetically engineered in order to express these receptors. The test cell according to the invention may for example be a dendritic cell, a cell deriving from lymphoid lines (preferentially a T lymphocyte) or myeloid lines (preferentially a macrophage), an epithelial cell or a fibroblast. Preferentially, the test cell according to the invention is selected from the group comprising Jurkat cells (notably described in Schneider et al. *Int. J. Cancer* (1997) 19(5): 621-6), for example the cell clone Jurkat E6-1 (ATCC No.: TIB-152), Jurkat-CCR5 cells (notably described in Alkhatib et al. (1996) *Science* 272: 1955-1958 and the AIDS reagent NIBSC, UK). Still more preferentially, the test cell according to the invention is a Jurkat-CCR5 cell.

The techniques allowing to infect a test cell according to the invention may be infected with an HIV virus are well known to one skilled in the art and are notably described in Barré-Sinoussi et al. ((1983) *Science* 220(4599): 868-71)).

The microRNA expression level or the target mRNA expression level in the test cells may be measured by any techniques known to one skilled in the art. Many methods are known which allow quantification of the RNAs, for example, methods based on reverse transcription PCRs (RT-PCR) using specific oligonucleotides of RNA sequences or methods allowing hybridization of these RNAs, duplicates or triplicates of these RNAs with probes under stringent conditions. When the expression level of the target mRNAs is measured, it is possible to carry out a RT-PCR or make specific cDNA chips with a single probe allowing reverse transcription of all the mRNAs. The probes according to the invention are preferentially deposited on microarrays. The stringent conditions may easily be determined by one skilled in the art. For example, the stringent conditions according to the invention may comprise a hybridization step for 10 to 20 hours, preferably 16 hours, at a temperature from 40 to 50° C., preferably at 50° C., in the presence of an ionic force equivalent to the one induced by a concentration of 500 mM to 2M of NaCl, preferably 1M of NaCl. Other products may also be added as buffer solutions, such as Tris or MES, EDTA, Tween and BSA (bovine serum albumin).

The thereby measured expression levels of the microRNAs or their target mRNAs in a test cell respectively infected with a first virus using a first co-receptor and with at least one other virus using another co-receptor, may allow identification of the microRNAs or their target mRNAs, the expression of which is modulated during the infection by each of the viruses as compared with uninfected cells. The identification of the microRNAs and of their target mRNAs, the expression of which is modulated during the infection with each of the viruses, may be achieved by comparing the expression levels of the miRNAs or of their target miRNAs, measured after infection with each of the viruses, with the expression level of said miRNAs or said target mRNAs in uninfected cells. Preferentially, in order that a microRNA or its target mRNAs be considered as having a modulated expression during the infection of test cells with a virus, this expression is increased or decreased compared with the expression in uninfected test cells by a log 2 of the ratio (expression of said miRNA in infected cells/expression of said miRNA in uninfected cells) greater than 0.5 or less than −0.5 respectively.

The microRNAs or their target mRNAs identified as having a modulated expression during infection with each of the viruses may then be compared in order to select the miRNAs or their target mRNAs, the expression of which is specifically modified by the use of a co-receptor by the virus.

By <<modification of the specific expression level of the use of a co-receptor>> according to the invention is meant a modification, increase or decrease of the expression sufficient to allow identification of the co-receptor used by the virus.

By <<uninfected test cells>> or <<cells uninfected by the virus from the patient>>, are meant cells having not been put into contact with a virus whatsoever but also cells infected by a virus, notably a retrovirus, the cell co-receptors of which are exhibited by the test cells but are distinct from the first co-receptor or from the at least one other co-receptor used by the virus for entering the test cell in the methods according to the invention. For example, this virus may be an HIV virus pseudotyped by an amphotropic envelope of the VSV type or the PFV-1 virus.

For example if the expression of an miRNA or of one of its target mRNAs is increased during an infection with a first HIV virus using the CXCR4 co-receptor in Jurkat-CCR5 cells (expressing CXCR4 and CCR5) as compared with the expression of the miRNA or of one of its target mRNAs in uninfected Jurkat-CCR5 cells and that the expression of this miRNA or of one of its target mRNAs is not increased during infection with a second HIV virus using the CCR5 co-receptor in Jurkat-CCR5 cells as compared with the expression of the miRNA or one of its target mRNAs in the uninfected Jurkat-CCR5 cells, then the increase in the expression of said miRNA or said target mRNA is specific to the use of the CXCR4 receptor by the HIV virus.

The present invention may also relate to an in vitro method for identifying microRNAs or their target mRNAs, the expression of which, during the infection of cells by a virus using a receptor and at least one cell co-receptor for entering the cell, is specifically modified depending on the cell co-receptor used by the virus used for its entry into the cells, comprising:

i) determining the expression levels of microRNAs in a test cell expressing the receptor, a first co-receptor and at least one other co-receptor, after infection with a first virus using the first co-receptor and with at least one other virus using another co-receptor, respectively;

ii) comparing the expression levels of the thereby determined microRNAs;

iii) identifying the microRNAs, for which the modification of the expression level is specific of the use of a co-receptor.

The thereby measured expression levels of the microRNAs or of their target mRNAs in a test cell after infection by a virus using a first co-receptor and by at least one other virus using another co-receptor respectively may then be directly compared with each other. This comparison then allows to identify the microRNAs or their target mRNAs, for which the modification of the expression is specific to the use of the first co-receptor or to at least one other co-receptor by the virus.

The methods according to the invention may also comprise an additional step allowing to identify the target mRNAs of the thus-identified characteristic microRNAs, for which the modification of the expression level is specific to the use of a co-receptor by a virus for entering a cell. The targets of the miRNAs may be identified in data bases, notably miRBase (http://microrna.sanger.ac.uk/ and notably described in Griffiths-Jones et al. (2008) *Nucleic Acids Res.* 36, Griffiths-Jones et al. (2006) *Nucleic Acids Res.* 34, Griffiths-Jones et al. (2004) *Nucleic Acids Research* 32) and TargetScan (http://www.targetscan.org/ and notably described in Lewis et al. (2005) *Cell* 120: 15-20, Grimson et al. (2007) *Molecular Cell* 27: 91-105, Friedman et al. (2009) *Genome Research* 19: 92-105).

The expression <<sample from the patient which may comprise the HIV virus>> comprises all the biological liquids or tissues from a patient and that may contain viruses, such as for example peripheral blood, genital mucosas, lymphoid tissues, cerebrospinal liquid, placenta or human breast milk. The sample may be directly in contact with the test cells. Preferentially, the viruses are extracted from the sample before contact with the host cells. For example, the viruses of the patient may derive from primary isolates from a biological sample and be obtained by any methods known to one skilled in the art, for example the isolation of the HIV viruses may be carried out by co-culture of lymphocytes from patients infected with HIV with lymphocytes of seronegative donors for HIV notably according to the technique described by Barre-Sinoussi et al ((1983) *Science* 220(4599):868-71). The peripheral blood of a patient infected by the HIV virus may also be treated so as to separate the plasma from the cells (as this is notably described by Fang et al. (1995) *Proc. Natl. Acad. Sci. USA* 92:12110-4).

In order to apply the method for identifying a cell co-receptor used by a virus using a cell receptor and at least one cell co-receptor for entering a cell in a patient, the expression level of at least one miRNA and/or at least one target mRNA of this miRNA is measured. Preferably this miRNA and/or its target mRNA was identified as having a modification of the expression level specific to the use by the virus of a co-receptor. Preferably, this miRNA and/or its target mRNA will have been identified by a method according to the invention.

In particular, the method for identifying viruses in a patient according to the invention may be used for identifying viruses using CXCR4 and/or CCR5. Preferably this miRNA and/or its target mRNA will then have been identified as having a modification of the expression level specific to the use by the HIV virus of the CXCR4 and/or CCR5 receptor. Preferably, this miRNA and/or its target mRNA will have been identified by the method for identifying miRNA according to the invention.

Preferentially, the method according to the invention is applied for identifying the presence or the absence of viruses using the CXCR4 co-receptor in a patient. The method according to the invention may also be carried out several times on samples coming from a same patient sampled at different moments over time in order to identify the occurrences of viruses using the CXCR4 receptor and to thereby monitore the development of the disease in this patient.

The predetermined value may be a single value such as for example an expression level or an average of expression levels of a given miRNA or of a given target mRNA.

For example, in order to identify a virus using a given co-receptor, the predetermined value may be the value of the expression of a given miRNA or of a given target mRNA in a cell expressing this co-receptor and infected with a reference virus known for using this co-receptor for entering the cell. For example, in order to identify viruses using CXCR4 and/or CCR5 in a patient, the predetermined value may be the value of the expression of a given miRNA or of a given target mRNA in a cell expressing CXCR4 or CCR5 after infection with a reference HIV virus using CXCR4 or CCR5 for entering a cell.

The comparison between the obtained expression level and the predetermined value allows to determine whether the investigated virus uses or not the same co-receptor as the reference virus for entering the cells. For example if the obtained value is close to the predetermined value, it is possible to infer that a co-receptor used by the tested virus is identical with the one used by the reference virus for entering the cells. By close value is preferentially meant values which do not differ by more than 50%, 40%, 30%, 20% or 10% and still more preferentially by less than 5%.

The reference value may also, for example, be the value of the expression of a given miRNA or a given target mRNA in an uninfected cell and therefore in the absence of infection by the virus of the patient. Preferably, it will have been shown beforehand that the expression of said miRNA or said target mRNA is modulated, increased or decreased specifically after infection of the cell with a reference virus using a given co-receptor as compared with the expression in an uninfected cell. The increase or the decrease of the expression value of an miRNA or of a target mRNA of the same nature as the one determined beforehand then indicates the use of a same co-receptor by the viruses. By the expression increased or decreased of the same nature, is preferentially meant values of a log 2 of the ratio (expression of said miRNA and/or of a target mRNA in infected cells/expression of said miRNA and/or target mRNA in uninfected cells) of the same sign (negative or positive respectively). The step for comparing the expression level with a determined value (iii) in the method for identifying a co-receptor used by a virus of an infected patient according to the invention is then preferentially applied by determining whether the expression level of at least one miRNA and/or at least one target mRNA of an miRNA is increased or decreased relatively to the expression level of at least one miRNA and/or at least one target mRNA of an miRNA in uninfected test cells.

For example, the measurement of the expression of one or more microRNAs or target mRNAs, for which the expression has been shown as being specifically modified (increased or decreased) by reference HIV viruses using the co-receptor CXCR4, in uninfected cells may be compared with measurements of the expression of said microRNAs or target mRNAs in cells after infection by viruses from a patient. In the case of the absence of predefined modulations of certain microRNAs, this test will identify that CXCR4 is not a co-receptor used by an HIV virus from the patient. Conversely, if the predefined modulations (increased or decreased) are observed, the tests will identify that CXCR4 is a co-receptor used by the HIV virus of the patient, it may be noted that such a virus may be a virus with double tropism for example which may use CCR5 and CXCR4.

The miRNA, the expression of which is determined, may for example be selected from the group consisting of hsa-miR-574-5p (notably of SEQ ID NO: 31, ugagugugugugu-gugagugugu), hsa-miR-663 (notably of SEQ ID NO: 32, aggcggggcgccgcgggaccgc), hsa-miR-149* (notably of SEQ ID NO: 33, agggagggacgggggcugugc), hsa-miR-575 (notably of SEQ ID NO: 34, gagccaguuggacaggagc), hsa-miR-638 (notably of SEQ ID NO: 35, agggaucgcgggcggguggcggccu), hsa-miR-181b (notably of SEQ ID NO: 36, aacauucauugcu-gucggugggu), hsa-let-7g (notably of SEQ ID NO: 37, ugag-guaguaguuuguacaguu), hsa-miR-30a (notably of SEQ ID NO: 38, uguaaacauccucgacuggaag), hsa-miR-148a (notably of SEQ ID NO: 39, ucagugcacuacagaacuuugu) et hsa-miR-9* (notably of SEQ ID NO: 40, auaaagcuagauaaccgaaagu). Preferentially, the mi-RNA for which the expression is determined is hsa-miR-638.

The miRNAs for which the expression is determined may also be allelic or polymorphic variants of sequences SEQ ID NOS: 31 to 40 as well as ortholog sequences present in other species deriving from miRNAs of sequences SEQ ID NOS: 31 to 40 and fulfilling the same function, in particular regulating the expression of the same target mRNAs. For example, these miRNAs may derive from miRNAs of sequences SEQ ID NOS: 31 to 40 by one or several mutations of nucleic acids.

The mRNA for which the expression is determined may, for example, be selected from the group consisting of target mRNAs of the miRNAs of SEQ ID NOS: 31 to 40 or of miRNAs derived from them. In particular, the target mRNAs may be identified in databases as described above.

For example, an increase in the expression of at least one miRNA selected from the group comprising hsa-miR574-5p, hsa-miR-663, hsa-miR-149*, hsa-miR-575, hsa-miR-638 or a decrease in the expression of at least one microRNA selected from the group comprising hsa-miR-181b, hsa-let-7g, hsa-miR-30a, hsa-miR-148a and hsa-miR-9* indicates that CXCR4 is a co-receptor used by an HIV virus of the patient. On the contrary, an absence of an increase in the expression of at least one miRNA selected from the group comprising hsa-miR574-5p, hsa-miR-663, hsa-miR-149*, hsa-miR-575, hsa-miR-638 or an absence of decrease in the expression of at least one microRNA selected from the group comprising hsa-miR-181b, hsa-let-7g, hsa-miR-30a, hsa-miR-148a et hsa-miR-9* indicates that CXCR4 is not a co-receptor used by a virus of the patient.

FIGURE

FIG. 1: Expression of hsa-miR-638 in response to the infection by primary HIV-1 Isolates with CXCR4, CCR5 tropism or viruses with double tropism (dual). Jurkat-CCR5 cells are infected with 4 DUAL isolates (dual 1, dual 2, dual 3, dual 4), 4 CXCR4 isolates (X4 1, X4 2, X4 3, X4 4) and 3 CCR5 isolates (R5 1, R5 2, R5 3). Three days after infection, the cells are lyzed and the RNAs are analyzed by RT-qPCR directed against hsa-miR-638. The expression of hsa-miR-638 in the infected cells is normalized by the expression of uninfected Jurkat R5 control cells (NI).

EXAMPLES

Material and Methods

Viruses and Cell Lines

The viruses used in this study are prototype HIV-1 NL4.3 and HIV-2 ROD viruses both using the co-receptor CXCR4, the virus HIV-1 NLAD8 using the co-receptor CCR5 and viruses stemming from primary isolates using the CXCR4 co-receptor (3 isolates called X4 1, X4 2, X4 3 et X4 4), using the CCR5 co-receptor (3 isolates called R5 1, R5 2 and R5 3) or which may use both co-receptors CXCR4 and CCR5 (4 isolates called dual 1, dual 2, dual 3 and dual 4) as well as another retrovirus PFV-1, using neither CD4, nor CXCR4 nor CCR5 for its entry.

Jurkat and Jurkat-CCR5 cell lines expressing CCR5 in a stable way are used.

Infection infection with prototype viruses

The Jurkat and Jurkat-CCR5 cells are infected during 3 days with two infectious doses of HIV-1 NL4.3, HIV-2 ROD in order to take into account the modulations related to the infection multiplicity. The Jurkat-CCR5 cells are infected for 3 days with HIV-1 NLAD8 or PFV-1.

infection with viruses stemming from primary isolates

Jurkat-CCR5 cells are infected during 3 days with the viruses X4 1, X4 2, X4 3 and X4 4, R5 1, R5 2, R5 3, dual 1, dual 2, dual 3 or dual 4. Uninfected Jurkat-CCR5 cells are used as a control (NI).

Analysis of the Expression of the microRNAs

Analysis per micro-RNA chip

Three days after infection with the prototype viruses, the RNAs are extracted and subject to analyses by microRNA chips (LC Sciences or Affymetrix).

Analysis of the expression of hsa-miR-638 by RT-PCR

Three days after infection by the viruses stemming from primary isolates, the cells are lyzed and the expression of hsa-miR-368 is analyzed by RT-qPCR. The expression of hsa-miR-368 in the infected cells is normalized relatively to the expression of hsa-miR-368 in uninfected Jurkat-CCR5 control cells (NI).

Results

Example 1

Identification of the microRNAs

Modulations of the expression of the microRNAs induced by the prototype viruses HIV-1 NL4.3 and HIV-2 ROD, both using the co-receptor CXCR4, were studied. In order to limit the inter-individual variations and to operate with an identical genetic background (and therefore a comparable list of microRNAs) these modulations are studied both during the infection of the Jurkat cell line and of the Jurkat line expressing CCR5. Three days after the infection, the RNAs of the Jurkat cells are extracted and subject to analysis with microRNA chips. Table 1 shows a sub-population of microRNAs both modulated by HIV-1 NL4.3 and HIV-2 ROD.

TABLE 1

Significant (p < 0.01) modulations of the list of cell microRNAs induced during infection with HIV-1 NL4.3 and HIV-2 ROD of Jurkat cells and Jurkat-CCR5 cells at 1 and 100 TCID50.

microRNAs, the expression of which is increased during infection with NL4.3 and ROD

| | |
|---|---|
| hsa-miR-574-5p | hsa-miR-575 |
| hsa-miR-663 | hsa-miR-638 |
| hsa-miR-149* | | microRNAs, the expression of which is decreased during infection with NL4.3 and ROD

| | |
|---|---|
| hsa-miR-181b | hsa-miR-374b |
| hsa-let-7g | hsa-miR-148a |
| hsa-miR-26b | hsa-miR-181d |
| hsa-let-7c | hsa-miR-9* |
| hsa-miR-7 | hsa-miR-98 |
| hsa-miR-30a | hsa-let-7e |
| hsa-miR-9 | |

The infection of Jurkat-CCR5 cells with HIV-1 NLAD8 (with R5 tropism, Table 2) and with the control retrovirus PFV-1 using neither CD4, neither CXCR4 neither CCR5 for its entry also causes modulations of the expression of microRNA.

TABLE 2

Significant (p < 0.01) modulations of the list of cell microRNAs induced during infection with HIV-1 NLAD8.

microRNAs, the expression of which is increased during infection with NLAD8

| | |
|---|---|
| hsa-miR-19a | hsa-miR-30b |
| hsa-miR-19b | hsa-miR-23b |
| hsa-miR-30e | hsa-miR-128 |
| hsa-miR-29a | hsa-miR-106a |
| hsa-miR-29c | hsa-miR-15a |
| hsa-miR-342-3p | hsa-miR-17 |
| hsa-miR-30c | hsa-miR-222 |
| hsa-miR-92b | hsa-miR-30d |
| hsa-miR-1280 | hsa-miR-93 |
| hsa-miR-16 | hsa-miR-150 |
| hsa-miR-18b | hsa-let-7i |
| hsa-miR-92a | hsa-miR-25 |
| hsa-miR-18a | hsa-miR-20b |
| hsa-miR-106b | hsa-let-7g |
| hsa-miR-23a | hsa-miR-191 |
| hsa-miR-20a | | microRNAS, the expression of which is decreased during infection with NLAD8

| | |
|---|---|
| hsa-let-7d | hsa-miR-923 |
| hsa-let-7a | hsa-miR-374b |
| hsa-miR-181b | hsa-miR-342-5p |
| hsa-miR-21 | hsa-miR-181d |
| hsa-miR-155 | hsa-miR-638 |
| hsa-miR-26b | hsa-let-7b |
| hsa-miR-1826 | hsa-miR-9 |
| hsa-miR-423-5p | hsa-miR-575 |
| hsa-miR-7 | hsa-miR-1246 |
| hsa-miR-320c | hsa-miR-98 |
| hsa-miR-130b | hsa-miR-149* |
| hsa-miR-182 | hsa-let-7e |
| hsa-miR-320b | hsa-miR-574-5p |
| hsa-miR-320d | hsa-miR-483-5p |
| hsa-let-7c | hsa-miR-375 |
| hsa-miR-1275 | hsa-miR-936 |
| hsa-miR-320a | |

By comparing these tables, it may be seen that the expression of nine microRNAs is systematically reduced during infection independently of the HIV and of its tropism. (Table 3). The expression of these microRNAs is not affected by the infection with PFV-1.

TABLE 3

Significant (p < 0.01) modulations of the list of cell microRNAs induced during infection with NL4.3, ROD and NLAD8. microRNAs, the expression of which is decreased during infection with NL4.3, ROD and NLAD8

| | |
|---|---|
| hsa-miR-181b | hsa-miR-374b |
| hsa-miR-26b | hsa-miR-181d |
| hsa-let-7c | hsa-miR-98 |
| hsa-miR-7 | hsa-let-7e |
| hsa-miR-9 | |

Moreover, the expression of 5 microRNAs is increased during infection with NL4.3 or ROD but is not increased during infection with NLAD8. Finally, the expression of 4 microRNAs is specifically decreased during infection with NL4.3 or ROD but is not decreased during infection with NLAD8. (Table 4). No microRNA, the expression of which is increased or decreased specifically during infection with NL4.3 or ROD is affected during infection with PFV-1.

TABLE 4

Significant (p < 0.01) modulations of the list of cell microRNAs specifically induced during infection with NL4.3 and ROD (Increased, microRNAs, the expression of which is increased during the infection, Decreased: microRNAs, the expression of which is decreased during the infection).

| Name of the microRNA | infection with NL4.3 or ROD | SEQ ID NO: |
|---|---|---|
| hsa-miR-574-5p | increased | 33 |
| hsa-miR-663 | increased | 34 |
| hsa-miR-149* | increased | 35 |
| hsa-miR-575 | increased | 36 |
| hsa-miR-638 | increased | 37 |
| hsa-miR-181b | decreased | 38 |
| hsa-let-7g | decreased | 39 |
| hsa-miR-30a | decreased | 40 |
| hsa-miR-148a | decreased | 41 |
| hsa-miR-9* | decreased | 42 |

These results illustrate the importance of the modulations of the list of cell microRNAs induced by the entry of the virus. These analyses also show the possibility, due to the methods according to the invention to distinguish the use of a certain type of co-receptor (here CXCR4 or CCR5) by the HIV on the basis of the changes in the cell list of microRNAs.

Example 2

In order to validate the thereby obtained results, Jurkat-CCR5 cells (expressing both the receptor CXCR4 and the receptor CCR5) are infected with viruses stemming from primary isolates using the co-receptor CXCR4 (X4 1, X4 2, X4 3 and X4 4), using the co-receptors CCR5 (R5 1, R5 2 and R5 3) or which may use both co-receptors CXCR4 and CCR5 (dual 1, dual 2, dual 3 and dual 4).

The expression of hsa-miR-638 in infected or uninfected (NI, control) cells is measured after 3 days. As expected and as indicated in FIG. 1, the expression of hsa-miR-638 is not modified in the uninfected cells. This expression is not statistically modified any more in cells infected with viruses only using CCR5 as a co-receptor for entering the cells (R5 1, R5 2 and R5 3) (FIG. 1). On the other hand, this expression is significantly increased in cells having been infected with a virus capable of using the CXCR4 co-receptor for entering the cells (X4 1, X4 2, X4 3, X4 4, dual 1, dual 2, dual 3 and dual 4) (FIG. 1).

These results indicate that only an infection involving the CXCR4 co-receptor induces an increase in the expression of hsa-miR-638.

These results therefore confirm the data obtained in Example 1 and prove, if necessary, that the expression level of this micro-RNA in an infected cell allows determination of the co-receptor used by the virus for infecting this cell and therefore allows identification of the tropism of this virus.

The invention claimed is:

1. An in vitro method for determining if a cell co-receptor is used by a virus using a cell receptor and at least one cell co-receptor for entering a cell, in a patient infected with the virus, comprising:
   i) putting a sample of the patient which contains the virus in contact with a test cell expressing a cell receptor of the virus and at least one cell co-receptor of the virus, wherein the use of said cell co-receptor by the virus specifically modulates the expression of at least one miRNA;
   ii) determining the expression level of said at least one miRNA and/or of at least one target mRNA of said at least one miRNA in the test cell;
   iii) comparing the expression level with a predetermined value, said predetermined value being:
      the expression level of said at least one miRNA and/or of said at least one target mRNA in a cell expressing said at least one co-receptor and infected with a reference virus using said at least one co-receptor for entering the cell, or
      the expression level of said at least one miRNA and/or of said at least one target mRNA in an uninfected cell expressing said at least one co-receptor; and
   iv) inferring therefrom whether the virus uses or not said at least one cell co-receptor expressed by said test cell, wherein the virus is the HIV virus, and wherein the test cell expresses the cell receptor CD4 and a cell co-receptor selected from the group consisting of CXCR4, CCR5, CCR3, CCR2, CCR1, CCR4, CCR8, CCR9, CXCR2, STRL33, V28, gpr1, gpr15 and ChemR23, and wherein said at least one miRNA is selected from the group consisting of hsa-miR574-5p, hsa-miR-663, hsa-miR-149*, hsa-miR-575, hsa-miR-638, hsa-miR-181b, hsa-let-7g, hsa-miR-30a, hsa-miR-148a and hsa-miR-9*.

2. The method according to claim 1, wherein the predetermined value is the expression level of said at least one miRNA or of said at least one target mRNA in an uninfected test cell.

3. The method according to claim 1, wherein the test cell expresses CXCR4.

4. The method according to claim 1, wherein an increase in the expression of at least one microRNA selected from the group comprising hsa-miR574-5p, hsa-miR-663, hsa-miR-149*, hsa-miR-575, hsa-miR-638 or a decrease in the expression of at least one microRNA selected from the group comprising hsa-miR-181b, hsa-let-7g, hsa-miR-30a, hsa-miR-148a and hsa-miR-9* indicates that CXCR4 is a co-receptor used by the HIV virus.

5. The method according to claim 1, wherein the expression level of the at least one microRNA or the amount of the at least one mRNA is measured by RT-PCR or by means of a microchip.

6. The method according to claim 1, wherein the test cells are selected from the group consisting of Jurkat cells and of Jurkat-CCR5 cells.

* * * * *

SEQUENCE LISTING

```
<160> NUMBER OF SEQ ID NOS: 40

<210> SEQ ID NO 1
<211> LENGTH: 4320
<212> TYPE: DNA
<213> ORGANISM: Homo sapiens
<220> FEATURE:
<221> NAME/KEY: CDS
<222> LOCATION: (1038)..(1052)
<220> FEATURE:
<221> NAME/KEY: CDS
<222> LOCATION: (3185)..(4225)

<400> SEQUENCE: 1
tttcatctct ccgggcttat ttgctggttt ctccgaatgc gggccttgtc tggttcacgc      60
tggatcccca acgcctagaa cagtgcgtgg cacgcagttc gtccttctat aaatatcgga     120
ctaaatgcat ctctgtgatg gtaataccca cacggtgttg tgagaatgaa tgagtgattc     180
tgtgcaagtt cctagtgatc tgttacaaaa agtactggtc gctaaattac tcttataata     240
aagcatactt ttaggataat aaagcactat tcgcgaattg gttaccgcta ttatgaaatt     300
actgagcaat acatatctac atctgatcag tctccagaat tatgccaaat cctaccttct     360
tctgaaagta tctcctaatt atctgcacct gaccctagtg atgctgtgaa tgtgcaagta     420
tagctacatc ctccgaagga aggatcttta ctccttttac ctcctgaatg ggctgcgtct     480
gctgaaagcg cgggggaatg ggcggttgga agcttggccc tacttccagc attgccgcct     540
actggttggg ttactccagc aagtcactcc ccttccctgg gcctcagtgt ctctactgta     600
gcattcccag gtctggaatt ccatccactt tagcaaggat ggacgcgcca cagagagacg     660
cgttcctagc ccgcgcttcc cacctgtctt caggcgcatc ccgcttccct caaacttagg     720
aaatgcctct gggaggtcct gtccggctcc ggactcacta ccgaccaccc gcaaacagca     780
gggtcccctg ggcttcccaa gccgcgcacc tctccgcccc gccccctgcgc cctccttcct     840 cgcgtctgcc cctctccccc accccgcctt ctccctcccc gccccagcgg cgcatgcgcc     900
gcgctcggag cgtgttttta taaaagtccg gccgcggcca gaaacttcag tttgttggct     960
gcggcagcag gtagcaaagt gacgccgagg gcctgagtgc tccagtagcc accgcatctg    1020
gagaaccagc ggttacc atg gag ggg atc agt gtaagtccag tttcaacctg           1072
                  Met Glu Gly Ile Ser
                    1               5 ctttgtcata aatgtacaaa cgtttgaact tagagcgcag ccctctccg agcgggcaga     1132 agcggccagg acattggagg tacccgtact ccaaaaaagg gtcaccgaaa ggagttttct     1192
tgaccatgcc tatatagtgc gggtgggtgg gggggagca ggattggaat cttttctct     1252 gtgagtcgag gagaaacgac tggaaagagc gttccagtgg ctgcatgtgt ctcccccttg     1312
agtcccgccg cgcgcggcgg cttgcacgct gttgcaaac gtaagaacat tctgtgcaca     1372
agtgcagaga aggcgtgcgc gctgcctcgg gactcagacc accggtctct tccttgggga     1432
agcggggatg tcttggagcg agttacattg tctgaattta gaggcggagg gcggcgtgcc     1492
tgggctgact tcccaggagg agattgcgcc cgctttaact tcggggttaa gcgcctggtg     1552
actgttcttg acactgggtg cgtgtttgtt aaactctgtg cggccgacgg agctgtgcca     1612
```

```
gtctcccagc acagtaggca gagggcggga gaggcgggtg gacccaccgc gccgatcctc    1672 tgagggatc gagtggtggc agcagctagg agttgatccg cccgcgcgct ttgggtttga    1732
gggggaaacc ttcccgccgt ccgaagcgcg cctcttcccc acggccgcga gtgggtcctg    1792
cagttcgaga gtttgggtc gtgcagaggt cagcggagtg gtttgacctc cccttttgaca    1852 ccgcgcagct gccagccctg agatttgcgc tccggggata ggagcgggta cggggtgagg    1912
ggcgggggcg gttaagaccg cacctgggct gccaggtcgc cgccgcgaag actggcaggt    1972
gcaagtgggg aaaccgtttg ctctctccg agtccagttg tgatgtttaa ccgtcggtgg    2032
tttccagaaa ccttttgaaa ccctcttgct agggagtttt tggtttcctg cagcggcgcg    2092
caattcaaag acgctcgcgg cggagccgcc cagtcgctcc ccagcaccct gtgggacaga    2152
gcctggcgtg tcgcccagcg gagccctgc agcgctgctt gcgggcggtt ggcgtgggtg    2212
tagtgggcag ccgcggcggc ccggggctgg acgacccggc ccccgcgtg cccaccgcct    2272 ggaggcttcc agctgcccac ctccggccgg gttaactgga tcagtggcgg ggtaatggga    2332
agccacccgg gagagtgagg aaatgaaact tgggcgagg accacgggtg cagacccgt    2392 taccttctcc acccaggaaa atgccccgct ccctaacgtc ccaaacgcgc caagtgataa    2452
acacgaggat ggcaagagac ccacacaccg gaggagcgcc cgcttggggg aggaggtgcc    2512
gtttgttcat tttctgacac tcccgcccaa tatacccaa gcaccgaagg gccttcgttt    2572
taagaccgca ttctctttac ccactacaag ttgcttgaag cccagaatgg tttgtattta    2632
ggcaggcgtg ggaaaattaa gttttttgcgc tttaggagaa tgagtctttg caacgccccc    2692
gccctccccc cgtgatcctc ccttctcccc tcttccctcc ctgggcgaaa aacttcttac    2752
aaaaagttaa tcactgcccc tcctagcagc acccaccca ccccccacgc gcctgggag    2812 tggcctcttt gtgtgtattt ttttttttcct cctaaggaag gttttttttc ttccctctag    2872 tgggcgggc agaggagtta gccaagatgt gactttgaaa ccctcagcgt ctcagtgccc    2932
ttttgttcta aacaaagaat tttgtaattg gttctaccaa agaaggatat aatgaagtca    2992
ctatgggaaa agatggggag gagagttgta ggattctaca ttaattctct tgtgccctta    3052
gcccactact tcagaatttc ctgaagaaag caagcctgaa ttggttttttt aaattgcttt    3112 aaaaattttt tttaactggg ttaatgcttg ctgaattgga agtgaatgtc cattcctttg    3172
cctcttttgc ag ata tac act tca gat aac tac acc gag gaa atg ggc tca    3223
              Ile Tyr Thr Ser Asp Asn Tyr Thr Glu Glu Met Gly Ser
                               10                  15 ggg gac tat gac tcc atg aag gaa ccc tgt ttc cgt gaa gaa aat gct    3271
Gly Asp Tyr Asp Ser Met Lys Glu Pro Cys Phe Arg Glu Glu Asn Ala
 20                  25                  30 aat ttc aat aaa atc ttc ctg ccc acc atc tac tcc atc atc ttc tta    3319
Asn Phe Asn Lys Ile Phe Leu Pro Thr Ile Tyr Ser Ile Ile Phe Leu
 35                  40                  45                  50 act ggc att gtg ggc aat gga ttg gtc atc ctg gtc atg ggt tac cag    3367
Thr Gly Ile Val Gly Asn Gly Leu Val Ile Leu Val Met Gly Tyr Gln
                 55                  60                  65 aag aaa ctg aga agc atg acg gac aag tac agg ctg cac ctg tca gtg    3415
Lys Lys Leu Arg Ser Met Thr Asp Lys Tyr Arg Leu His Leu Ser Val
             70                  75                  80 gcc gac ctc ctc ttt gtc atc acg ctt ccc ttc tgg gca gtt gat gcc    3463
Ala Asp Leu Leu Phe Val Ile Thr Leu Pro Phe Trp Ala Val Asp Ala
         85                  90                  95 gtg gca aac tgg tac ttt ggg aac ttc cta tgc aag gca gtc cat gtc    3511
Val Ala Asn Trp Tyr Phe Gly Asn Phe Leu Cys Lys Ala Val His Val
    100                 105                 110
```

```
atc tac aca gtc aac ctc tac agc agt gtc ctc atc ctg gcc ttc atc      3559
Ile Tyr Thr Val Asn Leu Tyr Ser Ser Val Leu Ile Leu Ala Phe Ile
115                 120                 125                 130 agt ctg gac cgc tac ctg gcc atc gtc cac gcc acc aac agt cag agg      3607
Ser Leu Asp Arg Tyr Leu Ala Ile Val His Ala Thr Asn Ser Gln Arg
            135                 140                 145 cca agg aag ctg ttg gct gaa aag gtg gtc tat gtt ggc gtc tgg atc      3655
Pro Arg Lys Leu Leu Ala Glu Lys Val Val Tyr Val Gly Val Trp Ile
        150                 155                 160 cct gcc ctc ctg ctg act att ccc gac ttc atc ttt gcc aac gtc agt      3703
Pro Ala Leu Leu Leu Thr Ile Pro Asp Phe Ile Phe Ala Asn Val Ser
    165                 170                 175 gag gca gat gac aga tat atc tgt gac cgc ttc tac ccc aat gac ttg      3751
Glu Ala Asp Asp Arg Tyr Ile Cys Asp Arg Phe Tyr Pro Asn Asp Leu
180                 185                 190 tgg gtg gtt gtg ttc cag ttt cag cac atc atg gtt ggc ctt atc ctg      3799
Trp Val Val Val Phe Gln Phe Gln His Ile Met Val Gly Leu Ile Leu
195                 200                 205                 210 cct ggt att gtc atc ctg tcc tgc tat tgc att atc atc tcc aag ctg      3847
Pro Gly Ile Val Ile Leu Ser Cys Tyr Cys Ile Ile Ile Ser Lys Leu
            215                 220                 225 tca cac tcc aag ggc cac cag aag cgc aag gcc ctc aag acc aca gtc      3895
Ser His Ser Lys Gly His Gln Lys Arg Lys Ala Leu Lys Thr Thr Val
        230                 235                 240 atc ctc atc ctg gct ttc ttc gcc tgt tgg ctg cct tac tac att ggg      3943
Ile Leu Ile Leu Ala Phe Phe Ala Cys Trp Leu Pro Tyr Tyr Ile Gly
    245                 250                 255 atc agc atc gac tcc ttc atc ctc ctg gaa atc atc aag caa ggg tgt      3991
Ile Ser Ile Asp Ser Phe Ile Leu Leu Glu Ile Ile Lys Gln Gly Cys
260                 265                 270 gag ttt gag aac act gtg cac aag tgg att tcc atc acc gag gcc cta      4039
Glu Phe Glu Asn Thr Val His Lys Trp Ile Ser Ile Thr Glu Ala Leu
275                 280                 285                 290 gct ttc ttc cac tgt tgt ctg aac ccc atc ctc tat gct ttc ctt gga      4087
Ala Phe Phe His Cys Cys Leu Asn Pro Ile Leu Tyr Ala Phe Leu Gly
            295                 300                 305 gcc aaa ttt aaa acc tct gcc cag cac gca ctc acc tct gtg agc aga      4135
Ala Lys Phe Lys Thr Ser Ala Gln His Ala Leu Thr Ser Val Ser Arg
        310                 315                 320 ggg tcc agc ctc aag atc ctc tcc aaa gga aag cga ggt gga cat tca      4183
Gly Ser Ser Leu Lys Ile Leu Ser Lys Gly Lys Arg Gly Gly His Ser
    325                 330                 335 tct gtt tcc act gag tct gag tct tca agt ttt cac tcc agc                  4225
Ser Val Ser Thr Glu Ser Glu Ser Ser Ser Phe His Ser Ser
340                 345                 350 taacacagat gtaaaagact tttttttata cgataaataa ctttttttta agttacacat      4285
ttttcagata taaaagactg accaatattg tacag                                 4320

<210> SEQ ID NO 2
<211> LENGTH: 352
<212> TYPE: PRT
<213> ORGANISM: Homo sapiens

<400> SEQUENCE: 2

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30
```

```
Asn Ala Asn Phe Asn Lys Ile Phe Leu Pro Thr Ile Tyr Ser Ile Ile
            35                  40                  45
Phe Leu Thr Gly Ile Val Gly Asn Gly Leu Val Ile Leu Val Met Gly
 50                  55                  60
Tyr Gln Lys Lys Leu Arg Ser Met Thr Asp Lys Tyr Arg Leu His Leu
 65                  70                  75                  80
Ser Val Ala Asp Leu Leu Phe Val Ile Thr Leu Pro Phe Trp Ala Val
                85                  90                  95
Asp Ala Val Ala Asn Trp Tyr Phe Gly Asn Phe Leu Cys Lys Ala Val
                100                 105                 110
His Val Ile Tyr Thr Val Asn Leu Tyr Ser Ser Val Leu Ile Leu Ala
            115                 120                 125
Phe Ile Ser Leu Asp Arg Tyr Leu Ala Ile Val His Ala Thr Asn Ser
130                 135                 140
Gln Arg Pro Arg Lys Leu Leu Ala Glu Lys Val Val Tyr Val Gly Val
145                 150                 155                 160
Trp Ile Pro Ala Leu Leu Leu Thr Ile Pro Asp Phe Ile Phe Ala Asn
                165                 170                 175
Val Ser Glu Ala Asp Asp Arg Tyr Ile Cys Asp Arg Phe Tyr Pro Asn
                180                 185                 190
Asp Leu Trp Val Val Val Phe Gln Phe Gln His Ile Met Val Gly Leu
            195                 200                 205
Ile Leu Pro Gly Ile Val Ile Leu Ser Cys Tyr Cys Ile Ile Ile Ser
            210                 215                 220
Lys Leu Ser His Ser Lys Gly His Gln Lys Arg Lys Ala Leu Lys Thr
225                 230                 235                 240
Thr Val Ile Leu Ile Leu Ala Phe Phe Ala Cys Trp Leu Pro Tyr Tyr
                245                 250                 255
Ile Gly Ile Ser Ile Asp Ser Phe Ile Leu Leu Glu Ile Ile Lys Gln
                260                 265                 270
Gly Cys Glu Phe Glu Asn Thr Val His Lys Trp Ile Ser Ile Thr Glu
            275                 280                 285
Ala Leu Ala Phe Phe His Cys Cys Leu Asn Pro Ile Leu Tyr Ala Phe
290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Ser Phe His Ser Ser
            340                 345                 350

<210> SEQ ID NO 3
<211> LENGTH: 1560
<212> TYPE: DNA
<213> ORGANISM: Homo sapiens
<220> FEATURE:
<221> NAME/KEY: CDS
<222> LOCATION: (358)..(1416)

<400> SEQUENCE: 3
cttcagatag attatatctg gagtgaagaa tcctgccacc tatgtatctg gcatagtatt     60
ctgtgtagtg ggatgagcag agaacaaaaa caaaataatc cagtgagaaa agcccgtaaa    120
taaaccttca gaccagagat ctattctcta gcttatttta agctcaactt aaaaagaaga    180
actgttctct gattcttttc gccttcaata cacttaatga tttaactcca ccctccttca    240
```

-continued

```
aaagaaacag catttcctac ttttatactg tctatatgat tgatttgcac agctcatctg      300
gccagaagag ctgagacatc cgttccccta caagaaactc tccccgggtg aacaag          357
```

| | | | | | | | | | | | | | | | | |
|---|---|---|---|---|---|---|---|---|---|---|---|---|---|---|---|---|
| atg | gat | tat | caa | gtg | tca | agt | cca | atc | tat | gac | atc | aat | tat | tat | aca | 405 |
| Met | Asp | Tyr | Gln | Val | Ser | Ser | Pro | Ile | Tyr | Asp | Ile | Asn | Tyr | Tyr | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcg | gag | ccc | tgc | caa | aaa | atc | aat | gtg | aag | caa | atc | gca | gcc | cgc | ctc | 453 |
| Ser | Glu | Pro | Cys | Gln | Lys | Ile | Asn | Val | Lys | Gln | Ile | Ala | Ala | Arg | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | cct | ccg | ctc | tac | tca | ctg | gtg | ttc | atc | ttt | ggt | ttt | gtg | ggc | aac | 501 |
| Leu | Pro | Pro | Leu | Tyr | Ser | Leu | Val | Phe | Ile | Phe | Gly | Phe | Val | Gly | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| atg | ctg | gtc | atc | ctc | atc | ctg | ata | aac | tgc | aaa | agg | ctg | aag | agc | atg | 549 |
| Met | Leu | Val | Ile | Leu | Ile | Leu | Ile | Asn | Cys | Lys | Arg | Leu | Lys | Ser | Met | |
| | 50 | | | | | 55 | | | | | 60 | | | | | |

| | | | | | | | | | | | | | | | | |
|---|---|---|---|---|---|---|---|---|---|---|---|---|---|---|---|---|
| act | gac | atc | tac | ctg | ctc | aac | ctg | gcc | atc | tct | gac | ctg | ttt | ttc | ctt | 597 |
| Thr | Asp | Ile | Tyr | Leu | Leu | Asn | Leu | Ala | Ile | Ser | Asp | Leu | Phe | Phe | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctt | act | gtc | ccc | ttc | tgg | gct | cac | tat | gct | gcc | gcc | cag | tgg | gac | ttt | 645 |
| Leu | Thr | Val | Pro | Phe | Trp | Ala | His | Tyr | Ala | Ala | Ala | Gln | Trp | Asp | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| gga | aat | aca | atg | tgt | caa | ctc | ttg | aca | ggg | ctc | tat | ttt | ata | ggc | ttc | 693 |
| Gly | Asn | Thr | Met | Cys | Gln | Leu | Leu | Thr | Gly | Leu | Tyr | Phe | Ile | Gly | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | tct | gga | atc | ttc | ttc | atc | atc | ctc | ctg | aca | atc | gat | agg | tac | ctg | 741 |
| Phe | Ser | Gly | Ile | Phe | Phe | Ile | Ile | Leu | Leu | Thr | Ile | Asp | Arg | Tyr | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| gct | gtc | gtc | cat | gct | gtg | ttt | gct | tta | aaa | gcc | agg | acg | gtc | acc | ttt | 789 |
| Ala | Val | Val | His | Ala | Val | Phe | Ala | Leu | Lys | Ala | Arg | Thr | Val | Thr | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| ggg | gtg | gtg | aca | agt | gtg | atc | act | tgg | gtg | gtg | gct | gtg | ttt | gcg | tct | 837 |
| Gly | Val | Val | Thr | Ser | Val | Ile | Thr | Trp | Val | Val | Ala | Val | Phe | Ala | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctc | cca | gga | atc | atc | ttt | acc | aga | tct | caa | aaa | gaa | ggt | ctt | cat | tac | 885 |
| Leu | Pro | Gly | Ile | Ile | Phe | Thr | Arg | Ser | Gln | Lys | Glu | Gly | Leu | His | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | tgc | agc | tct | cat | ttt | cca | tac | agt | cag | tat | caa | ttc | tgg | aag | aat | 933 |
| Thr | Cys | Ser | Ser | His | Phe | Pro | Tyr | Ser | Gln | Tyr | Gln | Phe | Trp | Lys | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | cag | aca | tta | aag | ata | gtc | atc | ttg | ggg | ctg | gtc | ctg | ccg | ctg | ctt | 981 |
| Phe | Gln | Thr | Leu | Lys | Ile | Val | Ile | Leu | Gly | Leu | Val | Leu | Pro | Leu | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| gtc | atg | gtc | atc | tgc | tac | tcg | gga | atc | cta | aaa | act | ctg | ctt | cgg | tgt | 1029 |
| Val | Met | Val | Ile | Cys | Tyr | Ser | Gly | Ile | Leu | Lys | Thr | Leu | Leu | Arg | Cys | |
| | 210 | | | | | 215 | | | | | 220 | | | | | |

| | | | | | | | | | | | | | | | | |
|---|---|---|---|---|---|---|---|---|---|---|---|---|---|---|---|---|
| cga | aat | gag | aag | aag | agg | cac | agg | gct | gtg | agg | ctt | atc | ttc | acc | atc | 1077 |
| Arg | Asn | Glu | Lys | Lys | Arg | His | Arg | Ala | Val | Arg | Leu | Ile | Phe | Thr | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atg | att | gtt | tat | ttt | ctc | ttc | tgg | gct | ccc | tac | aac | att | gtc | ctt | ctc | 1125 |
| Met | Ile | Val | Tyr | Phe | Leu | Phe | Trp | Ala | Pro | Tyr | Asn | Ile | Val | Leu | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| ctg | aac | acc | ttc | cag | gaa | ttc | ttt | ggc | ctg | aat | aat | tgc | agt | agc | tct | 1173 |
| Leu | Asn | Thr | Phe | Gln | Glu | Phe | Phe | Gly | Leu | Asn | Asn | Cys | Ser | Ser | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| aac | agg | ttg | gac | caa | gct | atg | cag | gtg | aca | gag | act | ctt | ggg | atg | acg | 1221 |
| Asn | Arg | Leu | Asp | Gln | Ala | Met | Gln | Val | Thr | Glu | Thr | Leu | Gly | Met | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| cac | tgc | tgc | atc | aac | ccc | atc | atc | tat | gcc | ttt | gtc | ggg | gag | aag | ttc | 1269 |
| His | Cys | Cys | Ile | Asn | Pro | Ile | Ile | Tyr | Ala | Phe | Val | Gly | Glu | Lys | Phe | |
| | 290 | | | | | 295 | | | | | 300 | | | | | |

```
aga aac tac ctc tta gtc ttc ttc caa aag cac att gcc aaa cgc ttc    1317
Arg Asn Tyr Leu Leu Val Phe Phe Gln Lys His Ile Ala Lys Arg Phe
305                 310                 315                 320 tgc aaa tgc tgt tct att ttc cag caa gag gct ccc gag cga gca agc    1365
Cys Lys Cys Cys Ser Ile Phe Gln Gln Glu Ala Pro Glu Arg Ala Ser
                325                 330                 335 tca gtt tac acc cga tcc act ggg gag cag gaa ata tct gtg ggc ttg    1413
Ser Val Tyr Thr Arg Ser Thr Gly Glu Gln Glu Ile Ser Val Gly Leu
            340                 345                 350 tga cacggactca agtgggctgg tgacccagtc agagttgtgc acatggctta         1466
gttttcatac acagcctggg ctggggtgg ggtgggagag gtctttttta aaggaagtt    1526 actgttatag agggtctaag attcatccat ttat                              1560

<210> SEQ ID NO 4
<211> LENGTH: 352
<212> TYPE: PRT
<213> ORGANISM: Homo sapiens

<400> SEQUENCE: 4

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
```

```
                275                 280                 285
His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350

<210> SEQ ID NO 5
<211> LENGTH: 5160
<212> TYPE: DNA
<213> ORGANISM: Homo sapiens
<220> FEATURE:
<221> NAME/KEY: CDS
<222> LOCATION: (4015)..(5082)

<400> SEQUENCE: 5
```

| | |
|---|---|
| ttcttcctaa atttatttac aaatgtaaca caattccacc caaacttatg ttttttataag | 60 |
| taattgagta gatgatccta aagtttaata aaacaaatgg ctctaatagg taagacattt | 120 |
| ggaaatgtat aatgaaaggg agttgcataa taagatcatc tatataaatc atctaataaa | 180 |
| tctacaataa aaagtgtctc tagcacagaa ataagatatc aatagaatat aaggtacaaa | 240 |
| atcagattca ggaacattaa agaatatacg acaaggtga tatttcaagc ccaaagggga | 300 |
| gaagatggtt attcaacaca tagtgtttta aaatttgtca gataagaatg agaggagga | 360 |
| ggctcctctc ctctgacccc agggaatgtg agaagagaca cagtggttat gaaaggaagc | 420 |
| agtcacacct gtggatccct accttcccca tcagagctag ggggcatgga gcgctctctg | 480 |
| ctaagatggg gaccccccaag gaatgtctcc ctgtggggca cttccttacc agatgggatg | 540 |
| gccagtgcgg ttaagttggt ggtcaggcag aaaaaaaaga tctagtttgt actcttgaga | 600 |
| gttcctcggt ttgttcatgg catgggcagg gagtcaagga gcagcagcct tgcctcagtg | 660 |
| cctaccagtg caggaaaagg tgcatagcct gggccagggc cagggccctg gtggaggcgt | 720 |
| agtggtaaca gagagggctc tccattccag cccaaggaag actaagaatg aatacctcat | 780 |
| gagtatatta gctacaaacc accacagcag gttccagaaa aaggctcagc gttggaacca | 840 |
| ggtcaccccc actcagcaga caccagtcat ataaatcaag gaccaacagg agacaggaac | 900 |
| accccttcc cactctgccc catgtctcaa gttgtagtgg cccttcctcc agatctctgc | 960 |
| caccatctta gaaggaaca ctgaaagaag aaactgaaat tataagctga cagcataaag | 1020 |
| aggatgagta aaacctaaaa tcattgttca aatgaatgaa tcaagagaag tttaaaccac | 1080 |
| tttggactaa aatgtgtgaa tccttttttcc tgctatccag cagatgagaa gctggtaaca | 1140 |
| gagaccaaaa tagtttggag actaaagaat cattgcacat ttcactgctg agttgtattg | 1200 |
| tgagtaattt tagttgacct cactttttgta aatcttgcac acgggcatcc atatctgcac | 1260 |
| agagatatgt taacagtggt aaatgctgca tgaggagatt gggtgatttt tactttcgtt | 1320 |
| tttgtgctct tctttcttat tgttcttact tatttacgat tacccctatcg ttttccaaaa | 1380 |
| tgtaaaaggc cattttgaaa gcctaattca aacctcttca ctattttgta tctaagtatt | 1440 |
| caccttgatt gagactgggt agacaggtga aaaccatatc aggttttttaa ttttttttaatt | 1500 |
| tttaattatt tatttatttta tttatttttt gagatggagt ctggctgtcg cccaggctgg | 1560 |
| agtgcagcgg cgtgatcaca gttcactgca gcctcaacct tctaggctca agggattctc | 1620 |

```
ccacctcagc cccccaagta gttgggacca cacgtatgcg ccaccatgcc tggctaattt    1680
cttattttt  tgtagagata ggatctcact atattgtcca ggctggtctt gaattcctgg    1740
gctcaggtga gcctcccacc tgggcctccc aaagtactgg gattacaggc atgagccaag    1800
gtcccctgcc catatgagat tttctgtctc tgatcccatg cagctagtaa tcaaggactt    1860
ggctgctgac tctggaggac ctgcatgctt tcttgagctg tgaacttcag tgctaaaagc    1920
tcataggcag ccctgaaacc caaaccaaaa ggttctatgg tttatcatcc cgatcatgtt    1980
gattttatag aaataacaca tgaattaaag acactaccct caaactgagc aaaacttaag    2040
taatttttt  aaagtttgac ctgtttttaa atcactcttg gagaaaaagg aaaataaata    2100
caaataatta acggtgaata caggctacta tacctttgtt ctccagaatt agcagttctg    2160
ttcttttctt gctttagatg ctgaagtgca aaggacact  ctgtgattgt acgtgtgtaa    2220
ctgacaaaat gtgtatttt  tttctcagct gctatggatt ggattatgct attatgaata    2280
agaatgctga tgggagcaca cacaaaccat tgttcctca  gtccatttc  ctcctcaaaa    2340
gcctggaatg tgccattgat cagtgggaga tgtacctgga cagacccatg aaaagagatc    2400
aacaagttcc acccaaggga ccctattttt cctaatttca tttgaaatgg cttctaattg    2460
tccttctttc attcctgctt cctaccagtt ttacagcttt ttctggtttc aaatgtgaac    2520
tcacatacac tctcattttt cctcatcaca accccaagtg acccaatggt cctcactttc    2580
gatataagta aaggaggctc tgcattaagg gcttgtccaa ggcacgcagc tgagaggcgc    2640
taggactggc tccatttcca tctctattct cactgacttt gactaccag  accccaaca    2700
tgtgggggcct cagtattcga tcaattattc tattaagaag caaaaacaat tccccgcatt   2760
ggccccagtt attaagcatt tctcagattt accttgagaa atgcccatcg gcctgtatat    2820
tcacatcttc acccttgtcc cttcctccta gaaaggagaa agtcagttgg atgccctctg    2880
aggaactagt gcatggctta actgtccttc catgactcct gccttatctg ttttctattt    2940
tcctcctttt ccaccgaagt ctataatctc aagaaaagca ggcactgcc  ttagggctcc    3000
tggcctaaga aatatcaagt ccagtgagaa atcccattga ctgacccctc ctgcttaccc    3060
ctttgtgatg gagaagctcc caggggtttg cttttttgcat gttaccaggc ctaactcagc    3120
atcaccaggg gcaagaaaag gaaagtaacc taaactaatg ctgcttataa ttgtaattat    3180
tgtaatagtt aattactgtg attgtacatg tgtaacagac aaaatgtgta ttttttttcac   3240
agctgctgtg gattggatta tgccatttgg aataagaatg ctgttaagag cacacaagcc    3300
aggttcctca agtccgtagc aaattttca aaagttaaat ttaaaaatca ctacatttga    3360
atctagtgac aggagaaatg gacatggata gagactaaag atctagccca aatttttatat   3420
ttacttgtta gaggattttg aacaaattac taaatttctt caaggttcaa tttccccatt    3480
aactataatg aatggctcat cattatgggg ccctggagaa gcataattac ttgtaattgt    3540
aataatcatt gttattatta ttatacatat tttgcttta  aatggataag gattttaag    3600
gtatatgtaa actgtaaaac ataaaatgca aaatgccgta agagacagta gtaataataa    3660
tgattattat attgttatca ttatctagcc tgtttttcc  tgttttgtat ttcttccttt    3720
aaatgctttc agaaatctgt atccccattc ttcaccacca ccccacaaca tttctgcttc    3780
ttttcccatg ccgggtcatg ctaactttga agcttcagc  tctttccttc ctcaatcctt    3840
ttcctggcac ctctgatatg cctttgaaa ttcatgttaa agaatcccta ggctgctatc     3900
acatgtggca tctttgttga gtacatgaat aaatcaactg gtgtgtttta cgaaggatga    3960
ttatgcttca ttgtgggatt gtattttct  tcttctatca cagggagaag tgaa atg      4017
```

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  |  |  | Met |  |
|  |  |  |  |  |  |  |  |  |  |  |  |  |  | 1 |  |
| aca | acc | tca | cta | gat | aca | gtt | gag | acc | ttt | ggt | acc | aca | tcc | tac | tat | 4065 |
| Thr | Thr | Ser | Leu | Asp | Thr | Val | Glu | Thr | Phe | Gly | Thr | Thr | Ser | Tyr | Tyr |
|  |  | 5 |  |  |  |  | 10 |  |  |  |  | 15 |  |  |  |
| gat | gac | gtg | ggc | ctg | ctc | tgt | gaa | aaa | gct | gat | acc | aga | gca | ctg | atg | 4113 |
| Asp | Asp | Val | Gly | Leu | Leu | Cys | Glu | Lys | Ala | Asp | Thr | Arg | Ala | Leu | Met |
|  |  |  | 20 |  |  |  |  | 25 |  |  |  |  | 30 |  |  |
| gcc | cag | ttt | gtg | ccc | ccg | ctg | tac | tcc | ctg | gtg | ttc | act | gtg | ggc | ctc | 4161 |
| Ala | Gln | Phe | Val | Pro | Pro | Leu | Tyr | Ser | Leu | Val | Phe | Thr | Val | Gly | Leu |
|  | 35 |  |  |  |  | 40 |  |  |  |  | 45 |  |  |  |  |
| ttg | ggc | aat | gtg | gtg | gtg | gtg | atg | atc | ctc | ata | aaa | tac | agg | agg | ctc | 4209 |
| Leu | Gly | Asn | Val | Val | Val | Val | Met | Ile | Leu | Ile | Lys | Tyr | Arg | Arg | Leu |
| 50 |  |  |  |  | 55 |  |  |  |  | 60 |  |  |  |  | 65 |
| cga | att | atg | acc | aac | atc | tac | ctg | ctc | aac | ctg | gcc | att | tcg | gac | ctg | 4257 |
| Arg | Ile | Met | Thr | Asn | Ile | Tyr | Leu | Leu | Asn | Leu | Ala | Ile | Ser | Asp | Leu |
|  |  |  | 70 |  |  |  |  | 75 |  |  |  |  | 80 |  |  |
| ctc | ttc | ctc | gtc | acc | ctt | cca | ttc | tgg | atc | cac | tat | gtc | agg | ggg | cat | 4305 |
| Leu | Phe | Leu | Val | Thr | Leu | Pro | Phe | Trp | Ile | His | Tyr | Val | Arg | Gly | His |
|  |  | 85 |  |  |  |  | 90 |  |  |  |  | 95 |  |  |  |
| aac | tgg | gtt | ttt | ggc | cat | ggc | atg | tgt | aag | ctc | ctc | tca | ggg | ttt | tat | 4353 |
| Asn | Trp | Val | Phe | Gly | His | Gly | Met | Cys | Lys | Leu | Leu | Ser | Gly | Phe | Tyr |
|  |  |  | 100 |  |  |  |  | 105 |  |  |  |  | 110 |  |  |
| cac | aca | ggc | ttg | tac | agc | gag | atc | ttt | ttc | ata | atc | ctg | ctg | aca | atc | 4401 |
| His | Thr | Gly | Leu | Tyr | Ser | Glu | Ile | Phe | Phe | Ile | Ile | Leu | Leu | Thr | Ile |
|  | 115 |  |  |  |  | 120 |  |  |  |  | 125 |  |  |  |  |
| gac | agg | tac | ctg | gcc | att | gtc | cat | gct | gtg | ttt | gcc | ctt | cga | gcc | cgg | 4449 |
| Asp | Arg | Tyr | Leu | Ala | Ile | Val | His | Ala | Val | Phe | Ala | Leu | Arg | Ala | Arg |
| 130 |  |  |  |  | 135 |  |  |  |  | 140 |  |  |  |  | 145 |
| act | gtc | act | ttt | ggt | gtc | atc | acc | agc | atc | gtc | acc | tgg | ggc | ctg | gca | 4497 |
| Thr | Val | Thr | Phe | Gly | Val | Ile | Thr | Ser | Ile | Val | Thr | Trp | Gly | Leu | Ala |
|  |  |  |  | 150 |  |  |  |  | 155 |  |  |  |  | 160 |  |
| gtg | cta | gca | gct | ctt | cct | gaa | ttt | atc | ttc | tat | gag | act | gaa | gag | ttg | 4545 |
| Val | Leu | Ala | Ala | Leu | Pro | Glu | Phe | Ile | Phe | Tyr | Glu | Thr | Glu | Glu | Leu |
|  |  | 165 |  |  |  |  | 170 |  |  |  |  | 175 |  |  |  |
| ttt | gaa | gag | act | ctt | tgc | agt | gct | ctt | tac | cca | gag | gat | aca | gta | tat | 4593 |
| Phe | Glu | Glu | Thr | Leu | Cys | Ser | Ala | Leu | Tyr | Pro | Glu | Asp | Thr | Val | Tyr |
|  |  | 180 |  |  |  |  | 185 |  |  |  |  | 190 |  |  |  |
| agc | tgg | agg | cat | ttc | cac | act | ctg | aga | atg | acc | atc | ttc | tgt | ctc | gtt | 4641 |
| Ser | Trp | Arg | His | Phe | His | Thr | Leu | Arg | Met | Thr | Ile | Phe | Cys | Leu | Val |
|  | 195 |  |  |  |  | 200 |  |  |  |  | 205 |  |  |  |  |
| ctc | cct | ctg | ctc | gtt | atg | gcc | atc | tgc | tac | aca | gga | atc | atc | aaa | acg | 4689 |
| Leu | Pro | Leu | Leu | Val | Met | Ala | Ile | Cys | Tyr | Thr | Gly | Ile | Ile | Lys | Thr |
| 210 |  |  |  |  | 215 |  |  |  |  | 220 |  |  |  |  | 225 |
| ctg | ctg | agg | tgc | ccc | agt | aaa | aaa | aag | tac | aag | gcc | atc | cgg | ctc | att | 4737 |
| Leu | Leu | Arg | Cys | Pro | Ser | Lys | Lys | Lys | Tyr | Lys | Ala | Ile | Arg | Leu | Ile |
|  |  |  |  | 230 |  |  |  |  | 235 |  |  |  |  | 240 |  |
| ttt | gtc | atc | atg | gcg | gtg | ttt | ttc | att | ttc | tgg | aca | ccc | tac | aat | gtg | 4785 |
| Phe | Val | Ile | Met | Ala | Val | Phe | Phe | Ile | Phe | Trp | Thr | Pro | Tyr | Asn | Val |
|  |  |  | 245 |  |  |  |  | 250 |  |  |  |  | 255 |  |  |
| gct | atc | ctt | ctc | tct | tcc | tat | caa | tcc | atc | tta | ttt | gga | aat | gac | tgt | 4833 |
| Ala | Ile | Leu | Leu | Ser | Ser | Tyr | Gln | Ser | Ile | Leu | Phe | Gly | Asn | Asp | Cys |
|  |  | 260 |  |  |  |  | 265 |  |  |  |  | 270 |  |  |  |
| gag | cgg | agc | aag | cat | ctg | gac | ctg | gtc | atg | ctg | gtg | aca | gag | gtg | atc | 4881 |
| Glu | Arg | Ser | Lys | His | Leu | Asp | Leu | Val | Met | Leu | Val | Thr | Glu | Val | Ile |
| 275 |  |  |  |  | 280 |  |  |  |  | 285 |  |  |  |  |  |
| gcc | tac | tcc | cac | tgc | tgc | atg | aac | ccg | gtg | atc | tac | gcc | ttt | gtt | gga | 4929 |
| Ala | Tyr | Ser | His | Cys | Cys | Met | Asn | Pro | Val | Ile | Tyr | Ala | Phe | Val | Gly |
| 290 |  |  |  |  | 295 |  |  |  |  | 300 |  |  |  |  | 305 |

```
gag agg ttc cgg aag tac ctg cgc cac ttc ttc cac agg cac ttg ctc    4977
Glu Arg Phe Arg Lys Tyr Leu Arg His Phe Phe His Arg His Leu Leu
            310                 315                 320 atg cac ctg ggc aga tac atc cca ttc ctt cct agt gag aag ctg gaa    5025
Met His Leu Gly Arg Tyr Ile Pro Phe Leu Pro Ser Glu Lys Leu Glu
        325                 330                 335 aga acc agc tct gtc tct cca tcc aca gca gag ccg gaa ctc tct att    5073
Arg Thr Ser Ser Val Ser Pro Ser Thr Ala Glu Pro Glu Leu Ser Ile
    340                 345                 350 gtg ttt tag gtcagatgca gaaaattgcc taaagaggaa ggaccaagga             5122
Val Phe
    355 gatgaagcaa acacattaag ccttccacac tcacctct                            5160

<210> SEQ ID NO 6
<211> LENGTH: 355
<212> TYPE: PRT
<213> ORGANISM: Homo sapiens

<400> SEQUENCE: 6

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Leu
        195                 200                 205

Val Leu Pro Leu Leu Val Met Ala Ile Cys Tyr Thr Gly Ile Ile Lys
    210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285
```

```
Ile Ala Tyr Ser His Cys Cys Met Asn Pro Val Ile Tyr Ala Phe Val
        290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 7
<211> LENGTH: 1680
<212> TYPE: DNA
<213> ORGANISM: Homo sapiens
<220> FEATURE:
<221> NAME/KEY: CDS
<222> LOCATION: (361)..(1485)

<400> SEQUENCE: 7
agaaacagga gcagatgtac agggtttgcc tgactcacac tcaaggttgc ataagcaaga      60
tttcaaaatt aatcctattc tggagacctc aacccaatgt acaatgttcc tgactggaaa    120
agaagaacta tattttcctg atttttttt tcaaatcttt accattagtt gccctgtatc    180
tccgccttca ctttctgcag gaaactttat ttcctacttc tgcatgccaa gtttctacct    240
ctagatctgt ttggttcagt tgctgagaag cctgacatac caggactgcc tgagacaagc    300
cacaagctga acagagaaag tggattgaac aaggacgcat tccccagta catccacaac    360 atg ctg tcc aca tct cgt tct cgg ttt atc aga aat acc aac gag agc    408
Met Leu Ser Thr Ser Arg Ser Arg Phe Ile Arg Asn Thr Asn Glu Ser
1               5                   10                  15 ggt gaa gaa gtc acc acc ttt ttt gat tat gat tac ggt gct ccc tgt    456
Gly Glu Glu Val Thr Thr Phe Phe Asp Tyr Asp Tyr Gly Ala Pro Cys
                20                  25                  30 cat aaa ttt gac gtg aag caa att ggg gcc caa ctc ctg cct ccg ctc    504
His Lys Phe Asp Val Lys Gln Ile Gly Ala Gln Leu Leu Pro Pro Leu
            35                  40                  45 tac tcg ctg gtg ttc atc ttt ggt ttt gtg ggc aac atg ctg gtc gtc    552
Tyr Ser Leu Val Phe Ile Phe Gly Phe Val Gly Asn Met Leu Val Val
        50                  55                  60 ctc atc tta ata aac tgc aaa aag ctg aag tgc ttg act gac att tac    600
Leu Ile Leu Ile Asn Cys Lys Lys Leu Lys Cys Leu Thr Asp Ile Tyr
65                  70                  75                  80 ctg ctc aac ctg gcc atc tct gat ctg ctt ttt ctt att act ctc cca    648
Leu Leu Asn Leu Ala Ile Ser Asp Leu Leu Phe Leu Ile Thr Leu Pro
                85                  90                  95 ttg tgg gct cac tct gct gca aat gag tgg gtc ttt ggg aat gca atg    696
Leu Trp Ala His Ser Ala Ala Asn Glu Trp Val Phe Gly Asn Ala Met
            100                 105                 110 tgc aaa tta ttc aca ggg ctg tat cac atc ggt tat ttt ggc gga atc    744
Cys Lys Leu Phe Thr Gly Leu Tyr His Ile Gly Tyr Phe Gly Gly Ile
        115                 120                 125 ttc ttc atc atc ctc ctg aca atc gat aga tac ctg gct att gtc cat    792
Phe Phe Ile Ile Leu Leu Thr Ile Asp Arg Tyr Leu Ala Ile Val His
    130                 135                 140 gct gtg ttt gct tta aaa gcc agg acg gtc acc ttt ggg gtg gtg aca    840
Ala Val Phe Ala Leu Lys Ala Arg Thr Val Thr Phe Gly Val Val Thr
145                 150                 155                 160
```

```
agt gtg atc acc tgg ttg gtg gct gtg ttt gct tct gtc cca gga atc       888
Ser Val Ile Thr Trp Leu Val Ala Val Phe Ala Ser Val Pro Gly Ile
            165                 170                 175 atc ttt act aaa tgc cag aaa gaa gat tct gtt tat gtc tgt ggc cct       936
Ile Phe Thr Lys Cys Gln Lys Glu Asp Ser Val Tyr Val Cys Gly Pro
                180                 185                 190 tat ttt cca cga gga tgg aat aat ttc cac aca ata atg agg aac att       984
Tyr Phe Pro Arg Gly Trp Asn Asn Phe His Thr Ile Met Arg Asn Ile
            195                 200                 205 ttg ggg ctg gtc ctg ccg ctg ctc atc atg gtc atc tgc tac tcg gga      1032
Leu Gly Leu Val Leu Pro Leu Leu Ile Met Val Ile Cys Tyr Ser Gly
        210                 215                 220 atc ctg aaa acc ctg ctt cgg tgt cga aac gag aag aag agg cat agg      1080
Ile Leu Lys Thr Leu Leu Arg Cys Arg Asn Glu Lys Lys Arg His Arg
225                 230                 235                 240 gca gtg aga gtc atc ttc acc atc atg att gtt tac ttt ctc ttc tgg      1128
Ala Val Arg Val Ile Phe Thr Ile Met Ile Val Tyr Phe Leu Phe Trp
                245                 250                 255 act ccc tat aat att gtc att ctc ctg aac acc ttc agg gaa ttc ttc      1176
Thr Pro Tyr Asn Ile Val Ile Leu Leu Asn Thr Phe Gln Glu Phe Phe
            260                 265                 270 ggc ctg agt aac tgt gaa agc acc agt caa ctg gac caa gcc acg cag      1224
Gly Leu Ser Asn Cys Glu Ser Thr Ser Gln Leu Asp Gln Ala Thr Gln
        275                 280                 285 gtg aca gag act ctt ggg atg act cac tgc tgc atc aat ccc atc atc      1272
Val Thr Glu Thr Leu Gly Met Thr His Cys Cys Ile Asn Pro Ile Ile
290                 295                 300 tat gcc ttc gtt ggg gag aag ttc aga agc ctt ttt cac ata gct ctt      1320
Tyr Ala Phe Val Gly Glu Lys Phe Arg Ser Leu Phe His Ile Ala Leu
305                 310                 315                 320 ggc tgt agg att gcc cca ctc caa aaa cca gtg tgt gga ggt cca gga      1368
Gly Cys Arg Ile Ala Pro Leu Gln Lys Pro Val Cys Gly Gly Pro Gly
                325                 330                 335 gtg aga cca gga aag aat gtg aaa gtg act aca caa gga ctc ctc gat      1416
Val Arg Pro Gly Lys Asn Val Lys Val Thr Thr Gln Gly Leu Leu Asp
            340                 345                 350 ggt cgt gga aaa gga aag tca att ggc aga gcc cct gaa gcc agt ctt      1464
Gly Arg Gly Lys Gly Lys Ser Ile Gly Arg Ala Pro Glu Ala Ser Leu
        355                 360                 365 cag gac aaa gaa gga gcc tag agacagaaat gacagatctc tgctttggaa         1515
Gln Asp Lys Glu Gly Ala
            370 atcacacgtc tggcttcaca gatgtgtgat tcacagtgtg aatcttggtg tctacgttac    1575 caggcaggaa ggctgagagg agagagactc cagctgggtt ggaaaacagt attttccaaa    1635 ctaccttcca gttcctcatt tttgaataca ggcatagagt tcaga                    1680

<210> SEQ ID NO 8
<211> LENGTH: 374
<212> TYPE: PRT
<213> ORGANISM: Homo sapiens

<400> SEQUENCE: 8

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45
```

```
Tyr Ser Leu Val Phe Ile Phe Gly Phe Val Gly Asn Met Leu Val Val
 50                  55                  60

Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Phe Leu Ile Thr Leu Pro
                 85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
            195                 200                 205

Leu Gly Leu Val Leu Pro Leu Leu Ile Met Val Ile Cys Tyr Ser Gly
210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
            355                 360                 365

Gln Asp Lys Glu Gly Ala
    370
```

<210> SEQ ID NO 9
<211> LENGTH: 1260
<212> TYPE: DNA
<213> ORGANISM: Homo sapiens
<220> FEATURE:
<221> NAME/KEY: CDS
<222> LOCATION: (72)..(1139)

<400> SEQUENCE: 9

```
ataaaaaccc agaaagcccc agaaacaaag acttcacgga caaagtccct tggaaccaga      60
gagaagccgg g atg gaa act cca aac acc aca gag gac tat gac acg acc     110
            Met Glu Thr Pro Asn Thr Thr Glu Asp Tyr Asp Thr Thr
              1               5                  10
```

```
aca gag ttt gac tat ggg gat gca act ccg tgc cag aag gtg aac gag      158
Thr Glu Phe Asp Tyr Gly Asp Ala Thr Pro Cys Gln Lys Val Asn Glu
    15                  20                  25 agg gcc ttt ggg gcc caa ctg ctg ccc cct ctg tac tcc ttg gta ttt      206
Arg Ala Phe Gly Ala Gln Leu Leu Pro Pro Leu Tyr Ser Leu Val Phe
30                  35                  40                  45 gtc att ggc ctg gtt gga aac atc ctg gtg gtc ctg gtc ctt gtg caa      254
Val Ile Gly Leu Val Gly Asn Ile Leu Val Val Leu Val Leu Val Gln
                50                  55                  60 tac aag agg cta aaa aac atg acc agc atc tac ctc ctg aac ctg gcc      302
Tyr Lys Arg Leu Lys Asn Met Thr Ser Ile Tyr Leu Leu Asn Leu Ala
            65                  70                  75 att tct gac ctg ctc ttc ctg ttc acg ctt ccc ttc tgg atc gac tac      350
Ile Ser Asp Leu Leu Phe Leu Phe Thr Leu Pro Phe Trp Ile Asp Tyr
        80                  85                  90 aag ttg aag gat gac tgg gtt ttt ggt gat gcc atg tgt aag atc ctc      398
Lys Leu Lys Asp Asp Trp Val Phe Gly Asp Ala Met Cys Lys Ile Leu
    95                  100                 105 tct ggg ttt tat tac aca ggc ttg tac agc gag atc ttt ttc atc atc      446
Ser Gly Phe Tyr Tyr Thr Gly Leu Tyr Ser Glu Ile Phe Phe Ile Ile
110                 115                 120                 125 ctg ctg acg att gac agg tac ctg gcc atc gtc cac gcc gtg ttt gcc      494
Leu Leu Thr Ile Asp Arg Tyr Leu Ala Ile Val His Ala Val Phe Ala
                130                 135                 140 ttg cgg gca cgg acc gtc act ttt ggt gtc atc acc agc atc atc att      542
Leu Arg Ala Arg Thr Val Thr Phe Gly Val Ile Thr Ser Ile Ile Ile
            145                 150                 155 tgg gcc ctg gcc atc ttg gct tcc atg cca ggc tta tac ttt tcc aag      590
Trp Ala Leu Ala Ile Leu Ala Ser Met Pro Gly Leu Tyr Phe Ser Lys
        160                 165                 170 acc caa tgg gaa ttc act cac cac acc tgc agc ctt cac ttt cct cac      638
Thr Gln Trp Glu Phe Thr His His Thr Cys Ser Leu His Phe Pro His
    175                 180                 185 gaa agc cta cga gag tgg aag ctg ttt cag gct ctg aaa ctg aac ctc      686
Glu Ser Leu Arg Glu Trp Lys Leu Phe Gln Ala Leu Lys Leu Asn Leu
190                 195                 200                 205 ttt ggg ctg gta ttg cct ttg ttg gtc atg atc atc tgc tac aca ggg      734
Phe Gly Leu Val Leu Pro Leu Leu Val Met Ile Ile Cys Tyr Thr Gly
                210                 215                 220 att ata aag att ctg cta aga cga cca aat gag aag aaa tcc aaa gct      782
Ile Ile Lys Ile Leu Leu Arg Arg Pro Asn Glu Lys Lys Ser Lys Ala
            225                 230                 235 gtc cgt ttg att ttt gtc atc atg atc atc ttt ttt ctc ttt tgg acc      830
Val Arg Leu Ile Phe Val Ile Met Ile Ile Phe Phe Leu Phe Trp Thr
        240                 245                 250 ccc tac aat ttg act ata ctt att tct gtt ttc caa gac ttc ctg ttc      878
Pro Tyr Asn Leu Thr Ile Leu Ile Ser Val Phe Gln Asp Phe Leu Phe
    255                 260                 265 acc cat gag tgt gag cag agc aga cat ttg gac ctg gct gtg caa gtg      926
Thr His Glu Cys Glu Gln Ser Arg His Leu Asp Leu Ala Val Gln Val
270                 275                 280                 285 acg gag gtg atc gcc tac acg cac tgc tgt gtc aac cca gtg atc tac      974
Thr Glu Val Ile Ala Tyr Thr His Cys Cys Val Asn Pro Val Ile Tyr
                290                 295                 300 gcc ttc gtt ggt gag agg ttc cgg aag tac ctg cgg cag ttg ttc cac     1022
Ala Phe Val Gly Glu Arg Phe Arg Lys Tyr Leu Arg Gln Leu Phe His
            305                 310                 315 agg cgt gtg gct gtg cac ctg gtt aaa tgg ctc ccc ttc ctc tcc gtg     1070
Arg Arg Val Ala Val His Leu Val Lys Trp Leu Pro Phe Leu Ser Val
```

```
            320              325              330
gac agg ctg gag agg gtc agc tcc aca tct ccc tcc aca ggg gag cat     1118
Asp Arg Leu Glu Arg Val Ser Ser Thr Ser Pro Ser Thr Gly Glu His
    335              340              345 gaa ctc tct gct ggg ttc tga ctcagaccat aggaggccaa cccaaaataa        1169
Glu Leu Ser Ala Gly Phe
350             355 gcaggcgtga cctgccaggc acactgagcc agcagcctgg ctctcccagc caggttctga   1229
ctcttggcac agcatggagt cacagccact t                                  1260

<210> SEQ ID NO 10
<211> LENGTH: 355
<212> TYPE: PRT
<213> ORGANISM: Homo sapiens

<400> SEQUENCE: 10

Met Glu Thr Pro Asn Thr Thr Glu Asp Tyr Asp Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65              70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300
```

```
Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
            340                 345                 350

Ala Gly Phe
        355

<210> SEQ ID NO 11
<211> LENGTH: 1380
<212> TYPE: DNA
<213> ORGANISM: Homo sapiens
<220> FEATURE:
<221> NAME/KEY: CDS
<222> LOCATION: (183)..(1265)

<400> SEQUENCE: 11
cgggggtttt gatcttcttc cccttctttt cttccccttc ttctttcctt cctccctccc    60
tctctcattt cccttctcct tctccctcag tctccacatt caacattgac aagtccattc   120
agaaaagcaa gctgcttctg gttgggccca gacctgcctt gaggagcctg tagagttaaa   180 aa atg aac ccc acg gat ata gca gat acc acc ctc gat gaa agc ata     227
   Met Asn Pro Thr Asp Ile Ala Asp Thr Thr Leu Asp Glu Ser Ile
   1               5                   10                  15 tac agc aat tac tat ctg tat gaa agt atc ccc aag cct tgc acc aaa    275
Tyr Ser Asn Tyr Tyr Leu Tyr Glu Ser Ile Pro Lys Pro Cys Thr Lys
                20                  25                  30 gaa ggc atc aag gca ttt ggg gag ctc ttc ctg ccc cca ctg tat tcc    323
Glu Gly Ile Lys Ala Phe Gly Glu Leu Phe Leu Pro Pro Leu Tyr Ser
            35                  40                  45 ttg gtt ttt gta ttt ggt ctg ctt gga aat tct gtg gtg gtt ctg gtc    371
Leu Val Phe Val Phe Gly Leu Leu Gly Asn Ser Val Val Val Leu Val
        50                  55                  60 ctg ttc aaa tac aag cgg ctc agg tcc atg act gat gtg tac ctg ctc    419
Leu Phe Lys Tyr Lys Arg Leu Arg Ser Met Thr Asp Val Tyr Leu Leu
65                  70                  75 aac ctt gcc atc tcg gat ctg ctc ttc gtg ttt tcc ctc cct ttt tgg    467
Asn Leu Ala Ile Ser Asp Leu Leu Phe Val Phe Ser Leu Pro Phe Trp
80                  85                  90                  95 ggc tac tat gca gca gac cag tgg gtt ttt ggg cta ggt ctg tgc aag    515
Gly Tyr Tyr Ala Ala Asp Gln Trp Val Phe Gly Leu Gly Leu Cys Lys
                100                 105                 110 atg att tcc tgg atg tac ttg gtg ggc ttt tac agt ggc ata ttc ttt    563
Met Ile Ser Trp Met Tyr Leu Val Gly Phe Tyr Ser Gly Ile Phe Phe
            115                 120                 125 gtc atg ctc atg agc att gat aga tac ctg gcg ata gtg cac gcg gtg    611
Val Met Leu Met Ser Ile Asp Arg Tyr Leu Ala Ile Val His Ala Val
        130                 135                 140 ttt tcc ttg agg gca agg acc ttg act tat ggg gtc atc acc agt ttg    659
Phe Ser Leu Arg Ala Arg Thr Leu Thr Tyr Gly Val Ile Thr Ser Leu
145                 150                 155 gct aca tgg tca gtg gct gtg ttc gcc tcc ctt cct ggc ttt ctg ttc    707
Ala Thr Trp Ser Val Ala Val Phe Ala Ser Leu Pro Gly Phe Leu Phe
160                 165                 170                 175 agc act tgt tat act gag cgc aac cat acc tac tgc aaa acc aag tac    755
Ser Thr Cys Tyr Thr Glu Arg Asn His Thr Tyr Cys Lys Thr Lys Tyr
                180                 185                 190 tct ctc aac tcc acg acg tgg aag gtt ctc agc tcc ctg gaa atc aac    803
Ser Leu Asn Ser Thr Thr Trp Lys Val Leu Ser Ser Leu Glu Ile Asn
```

-continued

```
                                 195                 200                 205
att ctc gga ttg gtg atc ccc tta ggg atc atg ctg ttt tgc tac tcc        851
Ile Leu Gly Leu Val Ile Pro Leu Gly Ile Met Leu Phe Cys Tyr Ser
            210                 215                 220 atg atc atc agg acc ttg cag cat tgt aaa aat gag aag aag aac aag        899
Met Ile Ile Arg Thr Leu Gln His Cys Lys Asn Glu Lys Lys Asn Lys
225                 230                 235 gcg gtg aag atg atc ttt gcc gtg gtg gtc ctc ttc ctt ggg ttc tgg        947
Ala Val Lys Met Ile Phe Ala Val Val Val Leu Phe Leu Gly Phe Trp
240                 245                 250                 255 aca cct tac aac ata gtg ctc ttc cta gag acc ctg gtg gag cta gaa        995
Thr Pro Tyr Asn Ile Val Leu Phe Leu Glu Thr Leu Val Glu Leu Glu
            260                 265                 270 gtc ctt cag gac tgc acc ttt gaa aga tac ttg gac tat gcc atc cag        1043
Val Leu Gln Asp Cys Thr Phe Glu Arg Tyr Leu Asp Tyr Ala Ile Gln
        275                 280                 285 gcc aca gaa act ctg gct ttt gtt cac tgc tgc ctt aat ccc atc atc        1091
Ala Thr Glu Thr Leu Ala Phe Val His Cys Cys Leu Asn Pro Ile Ile
    290                 295                 300 tac ttt ttt ctg ggg gag aaa ttt cgc aag tac atc cta cag ctc ttc        1139
Tyr Phe Phe Leu Gly Glu Lys Phe Arg Lys Tyr Ile Leu Gln Leu Phe
305                 310                 315 aaa acc tgc agg ggc ctt ttt gtg ctc tgc caa tac tgt ggg ctc ctc        1187
Lys Thr Cys Arg Gly Leu Phe Val Leu Cys Gln Tyr Cys Gly Leu Leu
320                 325                 330                 335 caa att tac tct gct gac acc ccc agc tca tct tac acg cag tcc acc        1235
Gln Ile Tyr Ser Ala Asp Thr Pro Ser Ser Ser Tyr Thr Gln Ser Thr
            340                 345                 350 atg gat cat gat ctt cat gat gct ctg tag gaaaaatgaa atggtgaaat          1285
Met Asp His Asp Leu His Asp Ala Leu
            355                 360 gcagagtcaa tgaactttc cacattcaga gcttacttta aaattggtat ttttaggtaa      1345
gagatccctg agccagtgtc aggaggaagg cttac                                1380

<210> SEQ ID NO 12
<211> LENGTH: 360
<212> TYPE: PRT
<213> ORGANISM: Homo sapiens

<400> SEQUENCE: 12

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
```

```
                 130                 135                 140
Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360

<210> SEQ ID NO 13
<211> LENGTH: 1320
<212> TYPE: DNA
<213> ORGANISM: Homo spaiens
<220> FEATURE:
<221> NAME/KEY: CDS
<222> LOCATION: (139)..(1206)

<400> SEQUENCE: 13
tttgtagtgg gaggatacct ccagagaggc tgctgctcat tgagctgcac tcacatgagg      60
atacagactt tgtgaagaag gaattggcaa cactgaaacc tccagaacaa aggctgtcac     120
taaggtcccg ctgccttg atg gat tat aca ctt gac ctc agt gtg aca aca       171
                    Met Asp Tyr Thr Leu Asp Leu Ser Val Thr Thr
                     1               5                  10 gtg acc gac tac tac tac cct gat atc ttc tca agc ccc tgt gat gcg       219
Val Thr Asp Tyr Tyr Tyr Pro Asp Ile Phe Ser Ser Pro Cys Asp Ala
            15                  20                  25 gaa ctt att cag aca aat ggc aag ttg ctc ctt gct gtc ttt tat tgc       267
Glu Leu Ile Gln Thr Asn Gly Lys Leu Leu Leu Ala Val Phe Tyr Cys
        30                  35                  40 ctc ctg ttt gta ttc agt ctt ctg gga aac agc ctg gtc atc ctg gtc       315
Leu Leu Phe Val Phe Ser Leu Leu Gly Asn Ser Leu Val Ile Leu Val
    45                  50                  55 ctt gtg gtc tgc aag aag ctg agg agc atc aca gat gta tac ctc ttg       363
Leu Val Val Cys Lys Lys Leu Arg Ser Ile Thr Asp Val Tyr Leu Leu
60                  65                  70                  75
```

```
aac ctg gcc ctg tct gac ctg ctt ttt gtc ttc tcc ttc ccc ttt cag      411
Asn Leu Ala Leu Ser Asp Leu Leu Phe Val Phe Ser Phe Pro Phe Gln
            80                  85                  90 acc tac tat ctg ctg gac cag tgg gtg ttt ggg act gta atg tgc aaa      459
Thr Tyr Tyr Leu Leu Asp Gln Trp Val Phe Gly Thr Val Met Cys Lys
        95                  100                 105 gtg gtg tct ggc ttt tat tac att ggc ttc tac agc agc atg ttt ttc      507
Val Val Ser Gly Phe Tyr Tyr Ile Gly Phe Tyr Ser Ser Met Phe Phe
            110                 115                 120 atc acc ctc atg agt gtg gac agg tac ctg gct gtt gtc cat gcc gtg      555
Ile Thr Leu Met Ser Val Asp Arg Tyr Leu Ala Val Val His Ala Val
        125                 130                 135 tat gcc cta aag gtg agg acg atc agg atg ggc aca acg ctg tgc ctg      603
Tyr Ala Leu Lys Val Arg Thr Ile Arg Met Gly Thr Thr Leu Cys Leu
140                 145                 150                 155 gca gta tgg cta acc gcc att atg gct acc atc cca ttg cta gtg ttt      651
Ala Val Trp Leu Thr Ala Ile Met Ala Thr Ile Pro Leu Leu Val Phe
            160                 165                 170 tac caa gtg gcc tct gaa gat ggt gtt cta cag tgt tat tca ttt tac      699
Tyr Gln Val Ala Ser Glu Asp Gly Val Leu Gln Cys Tyr Ser Phe Tyr
        175                 180                 185 aat caa cag act ttg aag tgg aag atc ttc acc aac ttc aaa atg aac      747
Asn Gln Gln Thr Leu Lys Trp Lys Ile Phe Thr Asn Phe Lys Met Asn
            190                 195                 200 att tta ggc ttg ttg atc cca ttc acc atc ttt atg ttc tgc tac att      795
Ile Leu Gly Leu Leu Ile Pro Phe Thr Ile Phe Met Phe Cys Tyr Ile
        205                 210                 215 aaa atc ctg cac cag ctg aag agg tgt caa aac cac aac aag acc aag      843
Lys Ile Leu His Gln Leu Lys Arg Cys Gln Asn His Asn Lys Thr Lys
220                 225                 230                 235 gcc atc agg ttg gtg ctc att gtg gtc att gca tct tta ctt ttc tgg      891
Ala Ile Arg Leu Val Leu Ile Val Val Ile Ala Ser Leu Leu Phe Trp
            240                 245                 250 gtc cca ttc aac gtg gtt ctt ttc ctc act tcc ttg cac agt atg cac      939
Val Pro Phe Asn Val Val Leu Phe Leu Thr Ser Leu His Ser Met His
        255                 260                 265 atc ttg gat gga tgt agc ata agc caa cag ctg act tat gcc acc cat      987
Ile Leu Asp Gly Cys Ser Ile Ser Gln Gln Leu Thr Tyr Ala Thr His
            270                 275                 280 gtc aca gaa atc att tcc ttt act cac tgc tgt gtg aac cct gtt atc     1035
Val Thr Glu Ile Ile Ser Phe Thr His Cys Cys Val Asn Pro Val Ile
        285                 290                 295 tat gct ttt gtt ggg gag aag ttc aag aaa cac ctc tca gaa ata ttt     1083
Tyr Ala Phe Val Gly Glu Lys Phe Lys Lys His Leu Ser Glu Ile Phe
300                 305                 310                 315 cag aaa agt tgc agc caa atc ttc aac tac cta gga aga caa atg cct     1131
Gln Lys Ser Cys Ser Gln Ile Phe Asn Tyr Leu Gly Arg Gln Met Pro
            320                 325                 330 agg gag agc tgt gaa aag tca tca tcc tgc cag cag cac tcc tcc cgt     1179
Arg Glu Ser Cys Glu Lys Ser Ser Ser Cys Gln Gln His Ser Ser Arg
        335                 340                 345 tcc tcc agc gta gac tac att ttg tga ggatcaatga agactaaata           1226
Ser Ser Ser Val Asp Tyr Ile Leu
            350             355 taaaaacat tttcttgaat ggcatgctag tagcagtgag caaaggtgtg ggtgtgaaag    1286
gtttccaaaa aaagttcagc atgaaggatg ccat                              1320

<210> SEQ ID NO 14
<211> LENGTH: 355
```

<212> TYPE: PRT
<213> ORGANISM: Homo spaiens

<400> SEQUENCE: 14

```
Met Asp Tyr Thr Leu Asp Leu Ser Val Thr Val Thr Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys Leu Leu Leu Ala Val Phe Tyr Cys Leu Leu Phe Val Phe
            35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser
65              70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
                100                 105                 110

Tyr Tyr Ile Gly Phe Tyr Ser Ser Met Phe Phe Ile Thr Leu Met Ser
            115                 120                 125

Val Asp Arg Tyr Leu Ala Val Val His Ala Val Tyr Ala Leu Lys Val
130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
                180                 185                 190

Lys Trp Lys Ile Phe Thr Asn Phe Lys Met Asn Ile Leu Gly Leu Leu
            195                 200                 205

Ile Pro Phe Thr Ile Phe Met Phe Cys Tyr Ile Lys Ile Leu His Gln
            210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
                260                 265                 270

Ser Ile Ser Gln Gln Leu Thr Tyr Ala Thr His Val Thr Glu Ile Ile
            275                 280                 285

Ser Phe Thr His Cys Cys Val Asn Pro Val Ile Tyr Ala Phe Val Gly
            290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
                340                 345                 350

Tyr Ile Leu
        355
```

<210> SEQ ID NO 15
<211> LENGTH: 1186
<212> TYPE: DNA
<213> ORGANISM: Homo sapiens

```
<220> FEATURE:
<221> NAME/KEY: CDS
<222> LOCATION: (60)..(1169)

<400> SEQUENCE: 15
tgtcccaggg agagttgcat cgccctccac agagcaggct tgcatctgac tgacccacc        59 atg aca ccc aca gac ttc aca agc cct att cct aac atg gct gat gac       107
Met Thr Pro Thr Asp Phe Thr Ser Pro Ile Pro Asn Met Ala Asp Asp
1               5                   10                  15 tat ggc tct gaa tcc aca tct tcc atg gaa gac tac gtt aac ttc aac       155
Tyr Gly Ser Glu Ser Thr Ser Ser Met Glu Asp Tyr Val Asn Phe Asn
            20                  25                  30 ttc act gac ttc tac tgt gag aaa aac aat gtc agg cag ttt gcg agc       203
Phe Thr Asp Phe Tyr Cys Glu Lys Asn Asn Val Arg Gln Phe Ala Ser
        35                  40                  45 cat ttc ctc cca ccc ttg tac tgg ctc gtg ttc atc gtg ggt gcc ttg       251
His Phe Leu Pro Pro Leu Tyr Trp Leu Val Phe Ile Val Gly Ala Leu
    50                  55                  60 ggc aac agt ctt gtt atc ctt gtc tac tgg tac tgc aca aga gtg aag       299
Gly Asn Ser Leu Val Ile Leu Val Tyr Trp Tyr Cys Thr Arg Val Lys
65                  70                  75                  80 acc atg acc gac atg ttc ctt ttg aat ttg gca att gct gac ctc ctc       347
Thr Met Thr Asp Met Phe Leu Leu Asn Leu Ala Ile Ala Asp Leu Leu
                85                  90                  95 ttt ctt gtc act ctt ccc ttc tgg gcc att gct gct gct gac cag tgg       395
Phe Leu Val Thr Leu Pro Phe Trp Ala Ile Ala Ala Ala Asp Gln Trp
            100                 105                 110 aag ttc cag acc ttc atg tgc aag gtg gtc aac agc atg tac aag atg       443
Lys Phe Gln Thr Phe Met Cys Lys Val Val Asn Ser Met Tyr Lys Met
        115                 120                 125 aac ttc tac agc tgt gtg ttg ctg atc atg tgc atc agc gtg gac agg       491
Asn Phe Tyr Ser Cys Val Leu Leu Ile Met Cys Ile Ser Val Asp Arg
    130                 135                 140 tac att gcc att gcc cag gcc atg aga gca cat act tgg agg gag aaa       539
Tyr Ile Ala Ile Ala Gln Ala Met Arg Ala His Thr Trp Arg Glu Lys
145                 150                 155                 160 agg ctt ttg tac agc aaa atg gtt tgc ttt acc atc tgg gta ttg gca       587
Arg Leu Leu Tyr Ser Lys Met Val Cys Phe Thr Ile Trp Val Leu Ala
                165                 170                 175 gct gct ctc tgc atc cca gaa atc tta tac agc caa atc aag gag gaa       635
Ala Ala Leu Cys Ile Pro Glu Ile Leu Tyr Ser Gln Ile Lys Glu Glu
            180                 185                 190 tcc ggc att gct atc tgc acc atg gtt tac cct agc gat gag agc acc       683
Ser Gly Ile Ala Ile Cys Thr Met Val Tyr Pro Ser Asp Glu Ser Thr
        195                 200                 205 aaa ctg aag tca gct gtc ttg acc ctg aag gtc att ctg ggg ttc ttc       731
Lys Leu Lys Ser Ala Val Leu Thr Leu Lys Val Ile Leu Gly Phe Phe
    210                 215                 220 ctt ccc ttc gtg gtc atg gct tgc tgc tat acc atc atc cac acc           779
Leu Pro Phe Val Val Met Ala Cys Cys Tyr Thr Ile Ile His Thr
225                 230                 235                 240 ctg ata caa gcc aag aag tct tcc aag cac aaa gcc cta aaa gtg acc       827
Leu Ile Gln Ala Lys Lys Ser Ser Lys His Lys Ala Leu Lys Val Thr
                245                 250                 255 atc act gtc ctg acc gtc ttt gtc ttg tct cag ttt ccc tac aac tgc       875
Ile Thr Val Leu Thr Val Phe Val Leu Ser Gln Phe Pro Tyr Asn Cys
            260                 265                 270 att ttg ttg gtg cag acc att gac gcc tat gcc atg ttc atc tcc aac       923
Ile Leu Leu Val Gln Thr Ile Asp Ala Tyr Ala Met Phe Ile Ser Asn
        275                 280                 285
```

```
tgt gcc gtt tcc acc aac att gac atc tgc ttc cag gtc acc cag acc    971
Cys Ala Val Ser Thr Asn Ile Asp Ile Cys Phe Gln Val Thr Gln Thr
    290                 295                 300 atc gcc ttc ttc cac agt tgc ctg aac cct gtt ctc tat gtt ttt gtg   1019
Ile Ala Phe Phe His Ser Cys Leu Asn Pro Val Leu Tyr Val Phe Val
305                 310                 315                 320 ggt gag aga ttc cgc cgg gat ctc gtg aaa acc ctg aag aac ttg ggt   1067
Gly Glu Arg Phe Arg Arg Asp Leu Val Lys Thr Leu Lys Asn Leu Gly
                325                 330                 335 tgc atc agc cag gcc cag tgg gtt tca ttt aca agg aga gag gga agc   1115
Cys Ile Ser Gln Ala Gln Trp Val Ser Phe Thr Arg Arg Glu Gly Ser
            340                 345                 350 ttg aag ctg tcg tct atg ttg ctg gag aca acc tca gga gca ctc tcc   1163
Leu Lys Leu Ser Ser Met Leu Leu Glu Thr Thr Ser Gly Ala Leu Ser
        355                 360                 365 ctc tga ggggtcttct ctgaggt                                        1186
Leu
```

```
<210> SEQ ID NO 16
<211> LENGTH: 369
<212> TYPE: PRT
<213> ORGANISM: Homo sapiens

<400> SEQUENCE: 16
```

```
Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
            20                  25                  30

Phe Thr Asp Phe Tyr Cys Glu Lys Asn Asn Val Arg Gln Phe Ala Ser
        35                  40                  45

His Phe Leu Pro Pro Leu Tyr Trp Leu Val Phe Ile Val Gly Ala Leu
    50                  55                  60

Gly Asn Ser Leu Val Ile Leu Val Tyr Trp Tyr Cys Thr Arg Val Lys
65                  70                  75                  80

Thr Met Thr Asp Met Phe Leu Leu Asn Leu Ala Ile Ala Asp Leu Leu
                85                  90                  95

Phe Leu Val Thr Leu Pro Phe Trp Ala Ile Ala Ala Asp Gln Trp
            100                 105                 110

Lys Phe Gln Thr Phe Met Cys Lys Val Val Asn Ser Met Tyr Lys Met
        115                 120                 125

Asn Phe Tyr Ser Cys Val Leu Leu Ile Met Cys Ile Ser Val Asp Arg
    130                 135                 140

Tyr Ile Ala Ile Ala Gln Ala Met Arg Ala His Thr Trp Arg Glu Lys
145                 150                 155                 160

Arg Leu Leu Tyr Ser Lys Met Val Cys Phe Thr Ile Trp Val Leu Ala
                165                 170                 175

Ala Ala Leu Cys Ile Pro Glu Ile Leu Tyr Ser Gln Ile Lys Glu Glu
            180                 185                 190

Ser Gly Ile Ala Ile Cys Thr Met Val Tyr Pro Ser Asp Glu Ser Thr
        195                 200                 205

Lys Leu Lys Ser Ala Val Leu Thr Leu Lys Val Ile Leu Gly Phe Phe
    210                 215                 220

Leu Pro Phe Val Val Met Ala Cys Cys Tyr Thr Ile Ile Ile His Thr
225                 230                 235                 240

Leu Ile Gln Ala Lys Lys Ser Ser Lys His Lys Ala Leu Lys Val Thr
                245                 250                 255
```

```
Ile Thr Val Leu Thr Val Phe Val Leu Ser Gln Phe Pro Tyr Asn Cys
                260                 265                 270
Ile Leu Leu Val Gln Thr Ile Asp Ala Tyr Ala Met Phe Ile Ser Asn
            275                 280                 285
Cys Ala Val Ser Thr Asn Ile Asp Ile Cys Phe Gln Val Thr Gln Thr
        290                 295                 300
Ile Ala Phe Phe His Ser Cys Leu Asn Pro Val Leu Tyr Val Phe Val
305                 310                 315                 320
Gly Glu Arg Phe Arg Arg Asp Leu Val Lys Thr Leu Lys Asn Leu Gly
                325                 330                 335
Cys Ile Ser Gln Ala Gln Trp Val Ser Phe Thr Arg Arg Glu Gly Ser
            340                 345                 350
Leu Lys Leu Ser Ser Met Leu Leu Glu Thr Thr Ser Gly Ala Leu Ser
        355                 360                 365
Leu

<210> SEQ ID NO 17
<211> LENGTH: 2400
<212> TYPE: DNA
<213> ORGANISM: Homo sapiens
<220> FEATURE:
<221> NAME/KEY: CDS
<222> LOCATION: (1178)..(2260)

<400> SEQUENCE: 17
caccctccac acccaggctt ccccagagca ggatctgtgc tgtccctgtg gcaagggcag      60
agccccagga gctagactaa atctgagagg aacaggggag tcaaggctag atggaggcac     120
acatgcagga caggaagggt ctccagcagg gctgaaagca ccaagcaagg gtagtgcaaa     180
ccctgtcttc tctgcttcct gctgcccctc tcttattggg tagcagactg gctgtgtctg     240
cttatcccgc atggtggcac atggctgccc agagctcccc aaataacctg ttacgttttcc    300 acccacaggg agaatcaggc agcccgcttg cttattgttt taatatact tttccaaact      360 acacagacat tcccaaagcg gtctccttc tacccaaaag agaaacgctg ggccttacta     420
attaactgaa gactctgcta gctcgagcct tccaaaactc catgccacaa ttgttcaaac     480
cattttccag aatacatctt taaaataac ttttagaaaa ttgaacaaag ggattcatgt      540
ctcagcttta tagtcaaacc atgatctttt ctgagggtat agcccatttg gagttcctgc     600
ttaatcccct gattaaaaac tgaatggggc tgagtgcagt gctcatgcct atattcccag     660
cactttggga gacagaggca ggagaattac ttaaggtcag gagtttaaga ccatcctgag     720
caacataaca agtccccatc tctaagacaa aaaaaaaga actgagtgac atctcacatc     780
tcacatttct gaacattaaa cccagccttg atagccaaag atgctcgcca ctgaaggatc     840
caggtagtat tgagggttct gtggggatta ccaaagaga actttctaca aagttttagg     900
tgatggcgat gctaaaagaa atgctaagaa tttctctctt atattaaaga aactatggt      960 cctctcataa aatgtaccat ttatcaccaa atttatctca taacctaaga gctaccactt    1020
acaaatttga agggaaaaat tactacattg taatactcaa gccaacacaa agaatccatat   1080 cccagtttct tgagtggatg ggcaagaata tggggaattt attatgcagt aaccttcatc    1140
tctcttctat aggtcaggat ttaagtttac ctcaaaa atg gaa gat ttt aac atg     1195
                                         Met Glu Asp Phe Asn Met
                                           1                   5 gag agt gac agc ttt gaa gat ttc tgg aaa ggt gaa gat ctt agt aat     1243
Glu Ser Asp Ser Phe Glu Asp Phe Trp Lys Gly Glu Asp Leu Ser Asn
```

```
tac agt tac agc tct acc ctg ccc cct ttt cta cta gat gcc gcc cca    1291
Tyr Ser Tyr Ser Ser Thr Leu Pro Pro Phe Leu Leu Asp Ala Ala Pro
         25                  30                  35 tgt gaa cca gaa tcc ctg gaa atc aac aag tat ttt gtg gtc att atc    1339
Cys Glu Pro Glu Ser Leu Glu Ile Asn Lys Tyr Phe Val Val Ile Ile
 40                  45                  50 tat gcc ctg gta ttc ctg ctg agc ctg ctg gga aac tcc ctc gtg atg    1387
Tyr Ala Leu Val Phe Leu Leu Ser Leu Leu Gly Asn Ser Leu Val Met
55                  60                  65                  70 ctg gtc atc tta tac agc agg gtc ggc cgc tcc gtc act gat gtc tac    1435
Leu Val Ile Leu Tyr Ser Arg Val Gly Arg Ser Val Thr Asp Val Tyr
                 75                  80                  85 ctg ctg aac cta gcc ttg gcc gac cta ctc ttt gcc ctg acc ttg ccc    1483
Leu Leu Asn Leu Ala Leu Ala Asp Leu Leu Phe Ala Leu Thr Leu Pro
         90                  95                 100 atc tgg gcc gcc tcc aag gtg aat ggc tgg att ttt ggc aca ttc ctg    1531
Ile Trp Ala Ala Ser Lys Val Asn Gly Trp Ile Phe Gly Thr Phe Leu
                105                 110                 115 tgc aag gtg gtc tca ctc ctg aag gaa gtc aac ttc tat agt ggc atc    1579
Cys Lys Val Val Ser Leu Leu Lys Glu Val Asn Phe Tyr Ser Gly Ile
120                 125                 130 ctg cta ctg gcc tgc atc agt gtg gac cgt tac ctg gcc att gtc cat    1627
Leu Leu Leu Ala Cys Ile Ser Val Asp Arg Tyr Leu Ala Ile Val His
135                 140                 145                 150 gcc aca cgc aca ctg acc cag aag cgc tac ttg gtc aaa ttc ata tgt    1675
Ala Thr Arg Thr Leu Thr Gln Lys Arg Tyr Leu Val Lys Phe Ile Cys
                155                 160                 165 ctc agc atc tgg ggt ctg tcc ttg ctc ctg gcc ctg cct gtc tta ctt    1723
Leu Ser Ile Trp Gly Leu Ser Leu Leu Leu Ala Leu Pro Val Leu Leu
                170                 175                 180 ttc cga agg acc gtc tac tca tcc aat gtt agc cca gcc tgc tat gag    1771
Phe Arg Arg Thr Val Tyr Ser Ser Asn Val Ser Pro Ala Cys Tyr Glu
                185                 190                 195 gac atg ggc aac aat aca gca aac tgg cgg atg ctg tta cgg atc ctg    1819
Asp Met Gly Asn Asn Thr Ala Asn Trp Arg Met Leu Leu Arg Ile Leu
200                 205                 210 ccc cag tcc ttt ggc ttc atc gtg cca ctg ctg atc atg ctg ttc tgc    1867
Pro Gln Ser Phe Gly Phe Ile Val Pro Leu Leu Ile Met Leu Phe Cys
215                 220                 225                 230 tac gga ttc acc ctg cgt acg ctg ttt aag gcc cac atg ggg cag aag    1915
Tyr Gly Phe Thr Leu Arg Thr Leu Phe Lys Ala His Met Gly Gln Lys
                235                 240                 245 cac cgg gcc atg cgg gtc atc ttt gct gtc gtc ctc atc ttc ctg ctc    1963
His Arg Ala Met Arg Val Ile Phe Ala Val Val Leu Ile Phe Leu Leu
                250                 255                 260 tgc tgg ctg ccc tac aac ctg gtc ctg ctg gca gac acc ctc atg agg    2011
Cys Trp Leu Pro Tyr Asn Leu Val Leu Leu Ala Asp Thr Leu Met Arg
            265                 270                 275 acc cag gtg atc cag gag acc tgt gag cgc cgc aat cac atc gac cgg    2059
Thr Gln Val Ile Gln Glu Thr Cys Glu Arg Arg Asn His Ile Asp Arg
280                 285                 290 gct ctg gat gcc acc gag att ctg ggc atc ctt cac agc tgc ctc aac    2107
Ala Leu Asp Ala Thr Glu Ile Leu Gly Ile Leu His Ser Cys Leu Asn
295                 300                 305                 310 ccc ctc atc tac gcc ttc att ggc cag aag ttt cgc cat gga ctc ctc    2155
Pro Leu Ile Tyr Ala Phe Ile Gly Gln Lys Phe Arg His Gly Leu Leu
                315                 320                 325 aag att cta gct ata cat ggc ttg atc agc aag gac tcc ctg ccc aaa    2203
```

```
Lys Ile Leu Ala Ile His Gly Leu Ile Ser Lys Asp Ser Leu Pro Lys
                    330                 335                 340 gac agc agg cct tcc ttt gtt ggc tct tct tca ggg cac act tcc act      2251
Asp Ser Arg Pro Ser Phe Val Gly Ser Ser Ser Gly His Thr Ser Thr
            345                 350                 355 act ctc taa gacctcctgc ctaagtgcag cccgtggggt tcctcccttc              2300
Thr Leu
    360 tcttcacagt cacattccaa gcctcatgtc cactggttct tcttggtctc agtgtcaatg    2360 cagcccccat tgtggtcaca ggaagtagag gaggccacgt                          2400

<210> SEQ ID NO 18
<211> LENGTH: 360
<212> TYPE: PRT
<213> ORGANISM: Homo sapiens

<400> SEQUENCE: 18

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
                20                  25                  30

Leu Leu Asp Ala Ala Pro Cys Glu Pro Glu Ser Leu Glu Ile Asn Lys
            35                  40                  45

Tyr Phe Val Val Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300
```

```
Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
            325                 330                 335

Lys Asp Ser Leu Pro Lys Asp Ser Arg Pro Ser Phe Val Gly Ser Ser
        340                 345                 350

Ser Gly His Thr Ser Thr Thr Leu
        355                 360

<210> SEQ ID NO 19
<211> LENGTH: 1029
<212> TYPE: DNA
<213> ORGANISM: Homo sapiens
<220> FEATURE:
<221> NAME/KEY: CDS
<222> LOCATION: (1)..(1029)

<400> SEQUENCE: 19 atg gca gag cat gat tac cat gaa gac tat ggg ttc agc agt ttc aat        48
Met Ala Glu His Asp Tyr His Glu Asp Tyr Gly Phe Ser Ser Phe Asn
1               5                   10                  15 gac agc agc cag gag gag cat caa gac ttc ctg cag ttc agc aag gtc        96
Asp Ser Ser Gln Glu Glu His Gln Asp Phe Leu Gln Phe Ser Lys Val
            20                  25                  30 ttt ctg ccc tgc atg tac ctg gtg gtg ttt gtc tgt ggt ctg gtg ggg       144
Phe Leu Pro Cys Met Tyr Leu Val Val Phe Val Cys Gly Leu Val Gly
        35                  40                  45 aac tct ctg gtg ctg gtc ata tcc atc ttc tac cat aag ttg cag agc       192
Asn Ser Leu Val Leu Val Ile Ser Ile Phe Tyr His Lys Leu Gln Ser
    50                  55                  60 ctg acg gat gtg ttc ctg gtg aac cta ccc ctg gct gac ctg gtg ttt       240
Leu Thr Asp Val Phe Leu Val Asn Leu Pro Leu Ala Asp Leu Val Phe
65                  70                  75                  80 gtc tgc act ctg ccc ttc tgg gcc tat gca ggc atc cat gaa tgg gtg       288
Val Cys Thr Leu Pro Phe Trp Ala Tyr Ala Gly Ile His Glu Trp Val
                85                  90                  95 ttt ggc cag gtc atg tgc aag agc cta ctg ggc atc tac act att aac       336
Phe Gly Gln Val Met Cys Lys Ser Leu Leu Gly Ile Tyr Thr Ile Asn
            100                 105                 110 ttc tac acg tcc atg ctc atc ctc acc tgc atc act gtg gat cgt ttc       384
Phe Tyr Thr Ser Met Leu Ile Leu Thr Cys Ile Thr Val Asp Arg Phe
        115                 120                 125 att gta gtg gtt aag gcc acc aag gcc tac aac cag caa gcc aag agg       432
Ile Val Val Val Lys Ala Thr Lys Ala Tyr Asn Gln Gln Ala Lys Arg
    130                 135                 140 atg acc tgg ggc aag gtc acc agc ttg ctc atc tgg gtg ata tcc ctg       480
Met Thr Trp Gly Lys Val Thr Ser Leu Leu Ile Trp Val Ile Ser Leu
145                 150                 155                 160 ctg gtt tcc ttg ccc caa att atc tat ggc aat gtc ttt aat ctc gac       528
Leu Val Ser Leu Pro Gln Ile Ile Tyr Gly Asn Val Phe Asn Leu Asp
                165                 170                 175 aag ctc ata tgt ggt tac cat gac gag gca att tcc act gtg gtt ctt       576
Lys Leu Ile Cys Gly Tyr His Asp Glu Ala Ile Ser Thr Val Val Leu
            180                 185                 190 gcc acc cag atg aca ctg ggg ttc ttc ttg cca ctg ctc acc atg att       624
Ala Thr Gln Met Thr Leu Gly Phe Phe Leu Pro Leu Leu Thr Met Ile
        195                 200                 205 gtc tgc tat tca gtc ata atc aaa aca ctg ctt cat gct gga ggc ttc       672
Val Cys Tyr Ser Val Ile Ile Lys Thr Leu Leu His Ala Gly Gly Phe
    210                 215                 220
```

```
cag aag cac aga tct cta aag atc atc ttc ctg gtg atg gct gtg ttc      720
Gln Lys His Arg Ser Leu Lys Ile Ile Phe Leu Val Met Ala Val Phe
225                 230                 235                 240 ctg ctg acc cag atg ccc ttc aac ctc atg aag ttc atc cgc agc aca      768
Leu Leu Thr Gln Met Pro Phe Asn Leu Met Lys Phe Ile Arg Ser Thr
            245                 250                 255 cac tgg gaa tac tat gcc atg acc agc ttt cac tac acc atc atg gtg      816
His Trp Glu Tyr Tyr Ala Met Thr Ser Phe His Tyr Thr Ile Met Val
        260                 265                 270 aca gag gcc atc gca tac ctg agg gcc tgc ctt aac cct gtg ctc tat      864
Thr Glu Ala Ile Ala Tyr Leu Arg Ala Cys Leu Asn Pro Val Leu Tyr
    275                 280                 285 gcc ttt gtc agc ctg aag ttt cga aag aac ttc tgg aaa ctt gtg aag      912
Ala Phe Val Ser Leu Lys Phe Arg Lys Asn Phe Trp Lys Leu Val Lys
290                 295                 300 gac att ggt tgc ctc cct tac ctt ggg gtc tca cat caa tgg aaa tct      960
Asp Ile Gly Cys Leu Pro Tyr Leu Gly Val Ser His Gln Trp Lys Ser
305                 310                 315                 320 tct gag gac aat tcc aag act ttt tct gcc tcc cac aat gtg gag gcc     1008
Ser Glu Asp Asn Ser Lys Thr Phe Ser Ala Ser His Asn Val Glu Ala
                325                 330                 335 acc agc atg ttc cag tta tag                                         1029
Thr Ser Met Phe Gln Leu
            340
```

<210> SEQ ID NO 20
<211> LENGTH: 342
<212> TYPE: PRT
<213> ORGANISM: Homo sapiens

<400> SEQUENCE: 20

```
Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205
```

```
Val Cys Tyr Ser Val Ile Ile Lys Thr Leu Leu His Ala Gly Gly Phe
            210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
            275                 280                 285

Ala Phe Val Ser Leu Lys Phe Arg Lys Asn Phe Trp Lys Leu Val Lys
            290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 21
<211> LENGTH: 1260
<212> TYPE: DNA
<213> ORGANISM: Homo sapiens
<220> FEATURE:
<221> NAME/KEY: CDS
<222> LOCATION: (93)..(1160)

<400> SEQUENCE: 21
gaaatactcg tctctggtaa agtctgagca ggacagggtg gctgactggc agatccagag      60
gttcccttgg cagtccacgc caggccttca cc atg gat cag ttc cct gaa tca     113
                                    Met Asp Gln Phe Pro Glu Ser
                                      1               5 gtg aca gaa aac ttt gag tac gat gat ttg gct gag gcc tgt tat att     161
Val Thr Glu Asn Phe Glu Tyr Asp Asp Leu Ala Glu Ala Cys Tyr Ile
         10                  15                  20 ggg gac atc gtg gtc ttt ggg act gtg ttc ctg tcc ata ttc tac tcc     209
Gly Asp Ile Val Val Phe Gly Thr Val Phe Leu Ser Ile Phe Tyr Ser
     25                  30                  35 gtc atc ttt gcc att ggc ctg gtg gga aat ttg ttg gta gtg ttt gcc     257
Val Ile Phe Ala Ile Gly Leu Val Gly Asn Leu Leu Val Val Phe Ala
 40                  45                  50                  55 ctc acc aac agc aag aag ccc aag agt gtc acc gac att tac ctc ctg     305
Leu Thr Asn Ser Lys Lys Pro Lys Ser Val Thr Asp Ile Tyr Leu Leu
                 60                  65                  70 aac ctg gcc ttg tct gat ctg ctg ttt gta gcc act ttg ccc ttc tgg     353
Asn Leu Ala Leu Ser Asp Leu Leu Phe Val Ala Thr Leu Pro Phe Trp
             75                  80                  85 act cac tat ttg ata aat gaa aag ggc ctc cac aat gcc atg tgc aaa     401
Thr His Tyr Leu Ile Asn Glu Lys Gly Leu His Asn Ala Met Cys Lys
         90                  95                 100 ttc act acc gcc ttc ttc ttc atc ggc ttt ttt gga agc ata ttc ttc     449
Phe Thr Thr Ala Phe Phe Phe Ile Gly Phe Phe Gly Ser Ile Phe Phe
    105                 110                 115 atc acc gtc atc agc att gat agg tac ctg gcc atc gtc ctg gcc gcc     497
Ile Thr Val Ile Ser Ile Asp Arg Tyr Leu Ala Ile Val Leu Ala Ala
120                 125                 130                 135 aac tcc atg aac aac cgg acc gtg cag cat ggc gtc acc atc agc cta     545
Asn Ser Met Asn Asn Arg Thr Val Gln His Gly Val Thr Ile Ser Leu
```

```
                    140                 145                 150
ggc gtc tgg gca gca gcc att ttg gtg gca gca ccc cag ttc atg ttc     593
Gly Val Trp Ala Ala Ala Ile Leu Val Ala Ala Pro Gln Phe Met Phe
            155                 160                 165 aca aag cag aaa gaa aat gaa tgc ctt ggt gac tac ccc gag gtc ctc     641
Thr Lys Gln Lys Glu Asn Glu Cys Leu Gly Asp Tyr Pro Glu Val Leu
        170                 175                 180 cag gaa atc tgg ccc gtg ctc cgc aat gtg gaa aca aat ttt ctt ggc     689
Gln Glu Ile Trp Pro Val Leu Arg Asn Val Glu Thr Asn Phe Leu Gly
    185                 190                 195 ttc cta ctc ccc ctg ctc att atg agt tat tgc tac ttc aga atc atc     737
Phe Leu Leu Pro Leu Leu Ile Met Ser Tyr Cys Tyr Phe Arg Ile Ile
200                 205                 210                 215 cag acg ctg ttt tcc tgc aag aac cac aag aaa gcc aaa gcc att aaa     785
Gln Thr Leu Phe Ser Cys Lys Asn His Lys Lys Ala Lys Ala Ile Lys
                220                 225                 230 ctg atc ctt ctg gtg gtc atc gtg ttt ctc ttc tgg aca ccc tac         833
Leu Ile Leu Leu Val Val Ile Val Phe Phe Leu Phe Trp Thr Pro Tyr
            235                 240                 245 aac gtt atg att ttc ctg gag acg ctt aag ctc tat gac ttc ttt ccc     881
Asn Val Met Ile Phe Leu Glu Thr Leu Lys Leu Tyr Asp Phe Phe Pro
        250                 255                 260 agt tgt gac atg agg aag gat ctg agg ctg gcc ctc agt gtg act gag     929
Ser Cys Asp Met Arg Lys Asp Leu Arg Leu Ala Leu Ser Val Thr Glu
    265                 270                 275 acg gtt gca ttt agc cat tgt tgc ctg aat cct ctc atc tat gca ttt     977
Thr Val Ala Phe Ser His Cys Cys Leu Asn Pro Leu Ile Tyr Ala Phe
280                 285                 290                 295 gct ggg gag aag ttc aga aga tac ctt tac cac ctg tat ggg aaa tgc    1025
Ala Gly Glu Lys Phe Arg Arg Tyr Leu Tyr His Leu Tyr Gly Lys Cys
                300                 305                 310 ctg gct gtc ctg tgt ggg cgc tca gtc cac gtt gat ttc tcc tca tct    1073
Leu Ala Val Leu Cys Gly Arg Ser Val His Val Asp Phe Ser Ser Ser
            315                 320                 325 gaa tca caa agg agc agg cat gga agt gtt ctg agc agc aat ttt act    1121
Glu Ser Gln Arg Ser Arg His Gly Ser Val Leu Ser Ser Asn Phe Thr
        330                 335                 340 tac cac acg agt gat gga gat gca ttg ctc ctt ctc tga aggaatccc      1170
Tyr His Thr Ser Asp Gly Asp Ala Leu Leu Leu Leu
    345                 350                 355 aaagccttgt gtctacagag aacctggagt tcctgaacct gatgctgact agtgaggaaa  1230
gatttttgtt gttatttctt acaggcacaa                                   1260

<210> SEQ ID NO 22
<211> LENGTH: 355
<212> TYPE: PRT
<213> ORGANISM: Homo sapiens

<400> SEQUENCE: 22

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
```

```
            65                  70                  75                  80
Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Ile Gly
            100                 105                 110

Phe Phe Gly Ser Ile Phe Ile Thr Val Ile Ser Ile Asp Arg Tyr
        115                 120                 125

Leu Ala Ile Val Leu Ala Ala Asn Ser Met Asn Asn Arg Thr Val Gln
130                 135                 140

His Gly Val Thr Ile Ser Leu Gly Val Trp Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 23
<211> LENGTH: 1560
<212> TYPE: DNA
<213> ORGANISM: Homo sapiens
<220> FEATURE:
<221> NAME/KEY: CDS
<222> LOCATION: (387)..(1454)

<400> SEQUENCE: 23
aacagattta cttaaccact ggcaaaccac atttcctttt ccagggcaat aacttaaaat      60
attatgtatt tcccttttgtt gcaaagagag gaaatacttc ttcctagact cagggcagct    120
gtgacccgtc ctcccagaga aatcattaaa ccacaaggat tcagacagag cccagagccc    180
tgaaaacttt ggccacgcac tttcccgcag cagccacagg caccggcaac ttcagagagc    240
cagataaaag tggaatgagg aatgcagccg ttctgaacac caccctccat ttcattctgg    300
aaccgggaag gtacacccag gcatgacaat agcttctctc ctcacagaaa tttaactgat    360
```

-continued

```
ttcttcattc tccatttagc aaggtc atg gaa gat ttg gag gaa aca tta ttt      413
                              Met Glu Asp Leu Glu Glu Thr Leu Phe
                              1               5 gaa gaa ttt gaa aac tat tcc tat gac cta gac tat tac tct ctg gag       461
Glu Glu Phe Glu Asn Tyr Ser Tyr Asp Leu Asp Tyr Tyr Ser Leu Glu
10              15              20              25 tct gat ttg gag gag aaa gtc cag ctg gga gtt gtt cac tgg gtc tcc       509
Ser Asp Leu Glu Glu Lys Val Gln Leu Gly Val Val His Trp Val Ser
                30              35              40 ctg gtg tta tat tgt ttg gct ttt gtt ctg gga att cca gga aat gcc       557
Leu Val Leu Tyr Cys Leu Ala Phe Val Leu Gly Ile Pro Gly Asn Ala
            45              50              55 atc gtc att tgg ttc acg ggg ttc aag tgg aag aag aca gtc acc act       605
Ile Val Ile Trp Phe Thr Gly Phe Lys Trp Lys Lys Thr Val Thr Thr
        60              65              70 ctg tgg ttc ctc aat cta gcc att gcg gat ttc att ttt ctt ctc ttt       653
Leu Trp Phe Leu Asn Leu Ala Ile Ala Asp Phe Ile Phe Leu Leu Phe
75              80              85 ctg ccc ctg tac atc tcc tat gtg gcc atg aat ttc cac tgg ccc ttt       701
Leu Pro Leu Tyr Ile Ser Tyr Val Ala Met Asn Phe His Trp Pro Phe
90              95              100             105 ggc atc tgg ctg tgc aaa gcc aat tcc ttc act gcc cag ttg aac atg       749
Gly Ile Trp Leu Cys Lys Ala Asn Ser Phe Thr Ala Gln Leu Asn Met
                110             115             120 ttt gcc agt gtt ttt ttc ctg aca gtg atc agc ctg gac cac tat atc       797
Phe Ala Ser Val Phe Phe Leu Thr Val Ile Ser Leu Asp His Tyr Ile
            125             130             135 cac ttg atc cat cct gtc tta tct cat cgg cat cga acc ctc aag aac       845
His Leu Ile His Pro Val Leu Ser His Arg His Arg Thr Leu Lys Asn
        140             145             150 tct ctg att gtc att ata ttc atc tgg ctt ttg gct tct cta att ggc       893
Ser Leu Ile Val Ile Ile Phe Ile Trp Leu Leu Ala Ser Leu Ile Gly
    155             160             165 ggt cct gcc ctg tac ttc cgg gac act gtg gag ttc aat aat cat act       941
Gly Pro Ala Leu Tyr Phe Arg Asp Thr Val Glu Phe Asn Asn His Thr
170             175             180             185 ctt tgc tat aac aat ttt cag aag cat gat cct gac ctc act ttg atc      989
Leu Cys Tyr Asn Asn Phe Gln Lys His Asp Pro Asp Leu Thr Leu Ile
            190             195             200 agg cac cat gtt ctg act tgg gtg aaa ttt atc att ggc tat ctc ttc      1037
Arg His His Val Leu Thr Trp Val Lys Phe Ile Ile Gly Tyr Leu Phe
        205             210             215 cct ttg cta aca atg agt att tgc tac ttg tgt ctc atc ttc aag gtg      1085
Pro Leu Leu Thr Met Ser Ile Cys Tyr Leu Cys Leu Ile Phe Lys Val
    220             225             230 aag aag cga agc atc ctg atc tcc agt agg cat ttc tgg aca att ctg      1133
Lys Lys Arg Ser Ile Leu Ile Ser Ser Arg His Phe Trp Thr Ile Leu
235             240             245 gtt gtt gtt gtg gcc ttt gtg gtt tgc tgg act cct tat cac ctg ttt      1181
Val Val Val Val Ala Phe Val Val Cys Trp Thr Pro Tyr His Leu Phe
250             255             260             265 agc att tgg gag ctc acc att cac cac aat agc tat tcc cac cat gtg      1229
Ser Ile Trp Glu Leu Thr Ile His His Asn Ser Tyr Ser His His Val
            270             275             280 atg cag gct gga atc ccc ctc tcc act ggt ttg gca ttc ctc aat agt      1277
Met Gln Ala Gly Ile Pro Leu Ser Thr Gly Leu Ala Phe Leu Asn Ser
        285             290             295 tgc ttg aac ccc atc ctt tat gtc cta att agt aag aag ttc caa gct      1325
Cys Leu Asn Pro Ile Leu Tyr Val Leu Ile Ser Lys Lys Phe Gln Ala
    300             305             310
```

```
cgc ttc cgg tcc tca gtt gct gag ata ctc aag tac aca ctg tgg gaa    1373
Arg Phe Arg Ser Ser Val Ala Glu Ile Leu Lys Tyr Thr Leu Trp Glu
    315                 320                 325 gtc agc tgt tct ggc aca gtg agt gaa cag ctc agg aac tca gaa acc    1421
Val Ser Cys Ser Gly Thr Val Ser Glu Gln Leu Arg Asn Ser Glu Thr
330                 335                 340                 345 aag aat ctg tgt ctc ctg gaa aca gct caa taa gttattactt ttccacaaat  1474
Lys Asn Leu Cys Leu Leu Glu Thr Ala Gln
                350                 355 cagtatatgg cttttttatgt gggtcctctg actgatgctt tcagattaaa attgtttcca  1534
agatagagag ccgactccac tttcat                                       1560

<210> SEQ ID NO 24
<211> LENGTH: 355
<212> TYPE: PRT
<213> ORGANISM: Homo sapiens

<400> SEQUENCE: 24

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ala
        35                  40                  45

Phe Val Leu Gly Ile Pro Gly Asn Ala Ile Val Ile Trp Phe Thr Gly
    50                  55                  60

Phe Lys Trp Lys Lys Thr Val Thr Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Ala Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Ser Ile Leu Ile
225                 230                 235                 240

Ser Ser Arg His Phe Trp Thr Ile Leu Val Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285
```

```
Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355

<210> SEQ ID NO 25
<211> LENGTH: 1083
<212> TYPE: DNA
<213> ORGANISM: Homo sapiens
<220> FEATURE:
<221> NAME/KEY: CDS
<222> LOCATION: (1)..(1083)

<400> SEQUENCE: 25
```

| | | | | | | | | | | | | | | | | |
|---|---|---|---|---|---|---|---|---|---|---|---|---|---|---|---|---|
| atg | gac | cca | gaa | gaa | act | tca | gtt | tat | ttg | gat | tat | tac | tat | gct | acg | 48 |
| Met | Asp | Pro | Glu | Glu | Thr | Ser | Val | Tyr | Leu | Asp | Tyr | Tyr | Tyr | Ala | Thr | |
| 1 | | | | 5 | | | | | 10 | | | | | 15 | | |
| agc | cca | aac | tct | gac | atc | agg | gag | acc | cac | tcc | cat | gtt | cct | tac | acc | 96 |
| Ser | Pro | Asn | Ser | Asp | Ile | Arg | Glu | Thr | His | Ser | His | Val | Pro | Tyr | Thr | |
| | | | 20 | | | | | 25 | | | | | 30 | | | |
| tct | gtc | ttc | ctt | cca | gtc | ttt | tac | aca | gct | gtg | ttc | ctg | act | gga | gtg | 144 |
| Ser | Val | Phe | Leu | Pro | Val | Phe | Tyr | Thr | Ala | Val | Phe | Leu | Thr | Gly | Val | |
| | | | 35 | | | | | 40 | | | | | 45 | | | |
| ctg | ggg | aac | ctt | gtt | ctc | atg | gga | gcg | ttg | cat | ttc | aaa | ccc | ggc | agc | 192 |
| Leu | Gly | Asn | Leu | Val | Leu | Met | Gly | Ala | Leu | His | Phe | Lys | Pro | Gly | Ser | |
| | 50 | | | | | 55 | | | | | 60 | | | | | |
| cga | aga | ctg | atc | gac | atc | ttt | atc | atc | aat | ctg | gct | gcc | tct | gac | ttc | 240 |
| Arg | Arg | Leu | Ile | Asp | Ile | Phe | Ile | Ile | Asn | Leu | Ala | Ala | Ser | Asp | Phe | |
| 65 | | | | | 70 | | | | | 75 | | | | | 80 | |
| att | ttt | ctt | gtc | aca | ttg | cct | ctc | tgg | gtg | gat | aaa | gaa | gca | tct | cta | 288 |
| Ile | Phe | Leu | Val | Thr | Leu | Pro | Leu | Trp | Val | Asp | Lys | Glu | Ala | Ser | Leu | |
| | | | | 85 | | | | | 90 | | | | | 95 | | |
| gga | ctg | tgg | agg | acg | ggc | tcc | ttc | ctg | tgc | aaa | ggg | agc | tcc | tac | atg | 336 |
| Gly | Leu | Trp | Arg | Thr | Gly | Ser | Phe | Leu | Cys | Lys | Gly | Ser | Ser | Tyr | Met | |
| | | | 100 | | | | | 105 | | | | | 110 | | | |
| atc | tcc | gtc | aat | atg | cac | tgc | agt | gtc | ctc | ctg | ctc | act | tgc | atg | agt | 384 |
| Ile | Ser | Val | Asn | Met | His | Cys | Ser | Val | Leu | Leu | Leu | Thr | Cys | Met | Ser | |
| | | | 115 | | | | | 120 | | | | | 125 | | | |
| gtt | gac | cgc | tac | ctg | gcc | att | gtg | tgg | cca | gtc | gta | tcc | agg | aaa | ttc | 432 |
| Val | Asp | Arg | Tyr | Leu | Ala | Ile | Val | Trp | Pro | Val | Val | Ser | Arg | Lys | Phe | |
| | 130 | | | | | 135 | | | | | 140 | | | | | |
| aga | agg | aca | gac | tgt | gca | tat | gta | gtc | tgt | gcc | agc | atc | tgg | ttt | atc | 480 |
| Arg | Arg | Thr | Asp | Cys | Ala | Tyr | Val | Val | Cys | Ala | Ser | Ile | Trp | Phe | Ile | |
| 145 | | | | | 150 | | | | | 155 | | | | | 160 | |
| tcc | tgc | ctg | ctg | ggg | ttg | cct | act | ctt | ctg | tcc | agg | gag | ctc | acg | ctg | 528 |
| Ser | Cys | Leu | Leu | Gly | Leu | Pro | Thr | Leu | Leu | Ser | Arg | Glu | Leu | Thr | Leu | |
| | | | | 165 | | | | | 170 | | | | | 175 | | |
| att | gat | gat | aag | cca | tac | tgt | gca | gag | aaa | aag | gca | act | cca | att | aaa | 576 |
| Ile | Asp | Asp | Lys | Pro | Tyr | Cys | Ala | Glu | Lys | Lys | Ala | Thr | Pro | Ile | Lys | |
| | | | 180 | | | | | 185 | | | | | 190 | | | |
| ctc | ata | tgg | tcc | ctg | gtg | gcc | tta | att | ttc | acc | ttt | ttt | gtc | cct | ttg | 624 |
| Leu | Ile | Trp | Ser | Leu | Val | Ala | Leu | Ile | Phe | Thr | Phe | Phe | Val | Pro | Leu | |
| | | | | 195 | | | | | 200 | | | | | 205 | | |
| ttg | agc | att | gtg | acc | tgc | tac | tgt | tgc | att | gca | agg | aag | ctg | tgt | gcc | 672 |

```
Leu Ser Ile Val Thr Cys Tyr Cys Cys Ile Ala Arg Lys Leu Cys Ala
        210                 215                 220 cat tac cag caa tca gga aag cac aac aaa aag ctg aag aaa tct ata     720
His Tyr Gln Gln Ser Gly Lys His Asn Lys Lys Leu Lys Lys Ser Ile
225                 230                 235                 240 aag atc atc ttt att gtc gtg gca gcc ttt ctt gtc tcc tgg ctg ccc     768
Lys Ile Ile Phe Ile Val Val Ala Ala Phe Leu Val Ser Trp Leu Pro
                245                 250                 255 ttc aat act ttc aag ttc ctg gcc att gtc tct ggg ttg cgg caa gaa     816
Phe Asn Thr Phe Lys Phe Leu Ala Ile Val Ser Gly Leu Arg Gln Glu
            260                 265                 270 cac tat tta ccc tca gct att ctt cag ctt ggt atg gag gtg agt gga     864
His Tyr Leu Pro Ser Ala Ile Leu Gln Leu Gly Met Glu Val Ser Gly
        275                 280                 285 ccc ttg gca ttt gcc aac agc tgt gtc aac cct ttc att tac tat atc     912
Pro Leu Ala Phe Ala Asn Ser Cys Val Asn Pro Phe Ile Tyr Tyr Ile
290                 295                 300 ttc gac agc tac atc cgc cgg gcc att gtc cac tgc ttg tgc cct tgc     960
Phe Asp Ser Tyr Ile Arg Arg Ala Ile Val His Cys Leu Cys Pro Cys
305                 310                 315                 320 ctg aaa aac tat gac ttt ggg agt agc act gag aca tca gat agt cac    1008
Leu Lys Asn Tyr Asp Phe Gly Ser Ser Thr Glu Thr Ser Asp Ser His
                325                 330                 335 ctc act aag gct ctc tcc acc ttc att cat gca gaa gat ttt gcc agg    1056
Leu Thr Lys Ala Leu Ser Thr Phe Ile His Ala Glu Asp Phe Ala Arg
            340                 345                 350 agg agg aag agg tct gtg tca ctc taa                                1083
Arg Arg Lys Arg Ser Val Ser Leu
        355                 360

<210> SEQ ID NO 26
<211> LENGTH: 360
<212> TYPE: PRT
<213> ORGANISM: Homo sapiens

<400> SEQUENCE: 26

Met Asp Pro Glu Glu Thr Ser Val Tyr Leu Asp Tyr Tyr Ala Thr
1               5                   10                  15

Ser Pro Asn Ser Asp Ile Arg Glu Thr His Ser His Val Pro Tyr Thr
                20                  25                  30

Ser Val Phe Leu Pro Val Phe Tyr Thr Ala Val Phe Leu Thr Gly Val
            35                  40                  45

Leu Gly Asn Leu Val Leu Met Gly Ala Leu His Phe Lys Pro Gly Ser
        50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Thr Cys Met Ser
        115                 120                 125

Val Asp Arg Tyr Leu Ala Ile Val Trp Pro Val Ser Arg Lys Phe
            130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175
```

```
Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Val Pro Leu
        195                 200                 205

Leu Ser Ile Val Thr Cys Tyr Cys Ile Ala Arg Lys Leu Cys Ala
210                 215                 220

His Tyr Gln Gln Ser Gly Lys His Asn Lys Leu Lys Lys Ser Ile
225                 230                 235                 240

Lys Ile Ile Phe Ile Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
            275                 280                 285

Pro Leu Ala Phe Ala Asn Ser Cys Val Asn Pro Phe Ile Tyr Tyr Ile
            290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
            355                 360

<210> SEQ ID NO 27
<211> LENGTH: 1680
<212> TYPE: DNA
<213> ORGANISM: Homo sapiens
<220> FEATURE:
<221> NAME/KEY: CDS
<222> LOCATION: (450)..(1592)

<400> SEQUENCE: 27
ggaaagccga cttgcaaaac cacagataat gttcagccca gcacagtagg ggtcaatttg      60
gtccacttgc tcagtgacaa aaagaaaaaa aaagtgggct gtcactaaag attttgactc     120
acaagagagg ggctggtctg gaggtgggag gaggagtga cgagtcaagg aggagacagg      180
gacgcaggag ggtgcaagga agtgtcttaa ctgagacggg ggtaaggcaa gagagggtgg     240
aggaaattct gcaggagaca ggcttcctcc agggtctgga gaacccagag gcagctcctc     300
ctgagtgctg ggaaggactc tgggcatctt cagcccttct tactctctga ggctcaagcc     360
agaaattcag gctgcttgca gagtgggtga cagagccacg gagctggtgt ccctgggacc     420
```
ctctgcccgt cttctctcca ctccccagc atg gag gaa ggt ggt gat ttt gac   473
                                Met Glu Glu Gly Gly Asp Phe Asp
                                  1               5 aac tac tat ggg gca gac aac cag tct gag tgt gag tac aca gac tgg   521
Asn Tyr Tyr Gly Ala Asp Asn Gln Ser Glu Cys Glu Tyr Thr Asp Trp
        10                  15                  20 aaa tcc tcg ggg gcc ctc atc cct gcc atc tac atg ttg gtc ttc ctc   569
Lys Ser Ser Gly Ala Leu Ile Pro Ala Ile Tyr Met Leu Val Phe Leu
 25                  30                  35                  40 ctg ggc acc acg ggc aac ggt ctg gtg ctc tgg acc gtg ttt cgg agc   617
Leu Gly Thr Thr Gly Asn Gly Leu Val Leu Trp Thr Val Phe Arg Ser
                 45                  50                  55 agc cgg gag aag agg cgc tca gct gat atc ttc att gct agc ctg gcg   665

```
              Ser Arg Glu Lys Arg Arg Ser Ala Asp Ile Phe Ile Ala Ser Leu Ala
                          60                  65                  70 gtg gct gac ctg acc ttc gtg gtg acg ctg ccc ctg tgg gct acc tac         713
Val Ala Asp Leu Thr Phe Val Val Thr Leu Pro Leu Trp Ala Thr Tyr
            75                  80                  85 acg tac cgg gac tat gac tgg ccc ttt ggg acc ttc ttc tgc aag ctc         761
Thr Tyr Arg Asp Tyr Asp Trp Pro Phe Gly Thr Phe Phe Cys Lys Leu
        90                  95                 100 agc agc tac ctc atc ttc gtc aac atg tac gcc agc gtc ttc tgc ctc         809
Ser Ser Tyr Leu Ile Phe Val Asn Met Tyr Ala Ser Val Phe Cys Leu
105                 110                 115                 120 acc ggc ctc agc ttc gac cgc tac ctg gcc atc gtg agg cca gtg gcc         857
Thr Gly Leu Ser Phe Asp Arg Tyr Leu Ala Ile Val Arg Pro Val Ala
                125                 130                 135 aat gct cgg ctg agg ctg cgg gtc agc ggg gcc gtg gcc acg gca gtt         905
Asn Ala Arg Leu Arg Leu Arg Val Ser Gly Ala Val Ala Thr Ala Val
            140                 145                 150 ctt tgg gtg ctg gcc gcc ctc ctg gcc atg cct gtc atg gtg tta cgc         953
Leu Trp Val Leu Ala Ala Leu Leu Ala Met Pro Val Met Val Leu Arg
        155                 160                 165 acc acc ggg gac ttg gag aac acc act aag gtg cag tgc tac atg gac        1001
Thr Thr Gly Asp Leu Glu Asn Thr Thr Lys Val Gln Cys Tyr Met Asp
170                 175                 180 tac tcc atg gtg gcc act gtg agc tca gag tgg gcc tgg gag gtg ggc        1049
Tyr Ser Met Val Ala Thr Val Ser Ser Glu Trp Ala Trp Glu Val Gly
185                 190                 195                 200 ctt ggg gtc tcg tcc acc acc gtg ggc ttt gtg gtg ccc ttc acc atc        1097
Leu Gly Val Ser Ser Thr Thr Val Gly Phe Val Val Pro Phe Thr Ile
                205                 210                 215 atg ctg acc tgt tac ttc ttc atc gcc caa acc atc gct ggc cac ttc        1145
Met Leu Thr Cys Tyr Phe Phe Ile Ala Gln Thr Ile Ala Gly His Phe
            220                 225                 230 cgc aag gaa cgc atc gag ggc ctg cgg aag cgg cgg ctg ctc agc            1193
Arg Lys Glu Arg Ile Glu Gly Leu Arg Lys Arg Arg Leu Leu Ser
        235                 240                 245 atc atc gtg gtg ctg gtg gtg acc ttt gcc ctg tgc tgg atg ccc tac        1241
Ile Ile Val Val Leu Val Val Thr Phe Ala Leu Cys Trp Met Pro Tyr
250                 255                 260 cac ctg gtg aag acg ctg tac atg ctg ggc agc ctg ctg cac tgg ccc        1289
His Leu Val Lys Thr Leu Tyr Met Leu Gly Ser Leu Leu His Trp Pro
265                 270                 275                 280 tgt gac ttt gac ctc ttc ctc atg aac atc ttc ccc tac tgc acc tgc        1337
Cys Asp Phe Asp Leu Phe Leu Met Asn Ile Phe Pro Tyr Cys Thr Cys
                285                 290                 295 atc agc tac gtc aac agc tgc ctc aac ccc ttc ctc tat gcc ttt ttc        1385
Ile Ser Tyr Val Asn Ser Cys Leu Asn Pro Phe Leu Tyr Ala Phe Phe
            300                 305                 310 gac ccc cgc ttc cgc cag gcc tgc acc tcc atg ctc tgc tgt ggc cag        1433
Asp Pro Arg Phe Arg Gln Ala Cys Thr Ser Met Leu Cys Cys Gly Gln
        315                 320                 325 agc agg tgc gca ggc acc tcc cac agc agc agt ggg gag aag tca gcc        1481
Ser Arg Cys Ala Gly Thr Ser His Ser Ser Ser Gly Glu Lys Ser Ala
330                 335                 340 agc tac tct tcg ggg cac agc cag ggg ccc ggc ccc aac atg ggc aag        1529
Ser Tyr Ser Ser Gly His Ser Gln Gly Pro Gly Pro Asn Met Gly Lys
345                 350                 355                 360 ggt gga gaa cag atg cac gag aaa tcc atc ccc tac agc cag gag acc        1577
Gly Gly Glu Gln Met His Glu Lys Ser Ile Pro Tyr Ser Gln Glu Thr
                365                 370                 375
```

```
                                                      -continued
ctt gtg gtt gac tag ggctgggagc agagagaagc ctggcgccct cggccctccc   1632
Leu Val Val Asp
            380 cggcctttgc ccttgctttc tgaaaatcag gtagtgtggc tactcctt              1680
```

<210> SEQ ID NO 28
<211> LENGTH: 380
<212> TYPE: PRT
<213> ORGANISM: Homo sapiens

<400> SEQUENCE: 28

```
Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350
```

```
Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 29
<211> LENGTH: 1560
<212> TYPE: DNA
<213> ORGANISM: Homo sapiens
<220> FEATURE:
<221> NAME/KEY: CDS
<222> LOCATION: (355)..(1476)

<400> SEQUENCE: 29
gaattcggca cgagccccgg cggccagcag ggagctcagg acagagcagg ctccctggga      60
agcctccggg tgataggggt gttccagctg cggcgctctg ggggttcaga gggggatctt     120
gaatgaacaa atgaatgaac tgctttctgg gcaaacagcc acagccagag gagcctgtga     180
ttggcagaaa gaagccaggg tgtgcaagtc tccccaacag cctcgagtgg cctgcagtca     240
cagggaaccc tcaggaagac cttccgggca gagaccagag ggtgtttcta gctgtgtaca     300
gggactgatt ggctgaggac tcacattgga gagctgcaga caacataacg gtga atg       357
                                                            Met
                                                             1 aga atg gag gat gaa gat tac aac act tcc atc agt tac ggt gat gaa       405
Arg Met Glu Asp Glu Asp Tyr Asn Thr Ser Ile Ser Tyr Gly Asp Glu
            5                   10                  15 tac cct gat tat tta gac tcc att gtg gtt ttg gag gac tta tcc ccc       453
Tyr Pro Asp Tyr Leu Asp Ser Ile Val Val Leu Glu Asp Leu Ser Pro
        20                  25                  30 ttg gaa gcc agg gtg acc agg atc ttc ctg gtg gtg gtc tac agc atc       501
Leu Glu Ala Arg Val Thr Arg Ile Phe Leu Val Val Val Tyr Ser Ile
    35                  40                  45 gtc tgc ttc ctc ggg att ctg ggc aat ggt ctg gtg atc atc att gcc       549
Val Cys Phe Leu Gly Ile Leu Gly Asn Gly Leu Val Ile Ile Ile Ala
50                  55                  60                  65 acc ttc aag atg aag aag aca gtg aac atg gtc tgg ttc ctc aac ctg       597
Thr Phe Lys Met Lys Lys Thr Val Asn Met Val Trp Phe Leu Asn Leu
                70                  75                  80 gca gtg gca gat ttc ctg ttc aac gtc ttc ctc cca atc cat atc acc       645
Ala Val Ala Asp Phe Leu Phe Asn Val Phe Leu Pro Ile His Ile Thr
            85                  90                  95 tat gcc gcc atg gac tac cac tgg gtt ttc ggg aca gcc atg tgc aag       693
Tyr Ala Ala Met Asp Tyr His Trp Val Phe Gly Thr Ala Met Cys Lys
        100                 105                 110 atc agc aac ttc ctt ctc atc cac aac atg ttc acc agc gtc ttc ctg       741
Ile Ser Asn Phe Leu Leu Ile His Asn Met Phe Thr Ser Val Phe Leu
    115                 120                 125 ctg acc atc atc agc tct gac cgc tgc atc tct gtg ctc ctc cct gtc       789
Leu Thr Ile Ile Ser Ser Asp Arg Cys Ile Ser Val Leu Leu Pro Val
130                 135                 140                 145 tgg tcc cag aac cac cgc agc gtt cgc ctg gct tac atg gcc tgc atg       837
Trp Ser Gln Asn His Arg Ser Val Arg Leu Ala Tyr Met Ala Cys Met
                150                 155                 160 gtc atc tgg gtc ctg gct ttc ttc ttg agt tcc cca tct ctc gtc ttc       885
Val Ile Trp Val Leu Ala Phe Phe Leu Ser Ser Pro Ser Leu Val Phe
            165                 170                 175 cgg gac aca gcc aac ctg cat ggg aaa ata tcc tgc ttc aac aac ttc       933
Arg Asp Thr Ala Asn Leu His Gly Lys Ile Ser Cys Phe Asn Asn Phe
        180                 185                 190
```

```
agc ctg tcc aca cct ggg tct tcc tcg tgg ccc act cac tcc caa atg      981
Ser Leu Ser Thr Pro Gly Ser Ser Ser Trp Pro Thr His Ser Gln Met
    195                 200                 205 gac cct gtg ggg tat agc cgg cac atg gtg gtg act gtc acc cgc ttc     1029
Asp Pro Val Gly Tyr Ser Arg His Met Val Val Thr Val Thr Arg Phe
210                 215                 220                 225 ctc tgt ggc ttc ctg gtc cca gtc ctc atc atc aca gct tgc tac ctc     1077
Leu Cys Gly Phe Leu Val Pro Val Leu Ile Ile Thr Ala Cys Tyr Leu
                230                 235                 240 acc atc gtc tgc aaa ctg cac cgc aac cgc ctg gcc aag acc aag aag     1125
Thr Ile Val Cys Lys Leu His Arg Asn Arg Leu Ala Lys Thr Lys Lys
            245                 250                 255 ccc ttc aag att att gtg acc atc atc att acc ttc ttc ctc tgc tgg     1173
Pro Phe Lys Ile Ile Val Thr Ile Ile Ile Thr Phe Phe Leu Cys Trp
        260                 265                 270 tgc ccc tac cac aca ctc aac ctc cta gag ctc cac cac act gcc atg     1221
Cys Pro Tyr His Thr Leu Asn Leu Leu Glu Leu His His Thr Ala Met
    275                 280                 285 cct ggc tct gtc ttc agc ctg ggt ttg ccc ctg gcc act gcc ctt gcc     1269
Pro Gly Ser Val Phe Ser Leu Gly Leu Pro Leu Ala Thr Ala Leu Ala
290                 295                 300                 305 att gcc aac agc tgc atg aac ccc att ctg tat gtt ttc atg ggt cag     1317
Ile Ala Asn Ser Cys Met Asn Pro Ile Leu Tyr Val Phe Met Gly Gln
                310                 315                 320 gac ttc aag aag ttc aag gtg gcc ctc ttc tct cgc ctg gtc aat gct     1365
Asp Phe Lys Lys Phe Lys Val Ala Leu Phe Ser Arg Leu Val Asn Ala
            325                 330                 335 cta agt gaa gat aca ggc cac tct tcc tac ccc agc cat aga agc ttt     1413
Leu Ser Glu Asp Thr Gly His Ser Ser Tyr Pro Ser His Arg Ser Phe
        340                 345                 350 acc aag atg tca tca atg aat gag agg act tct atg aat gag agg gag     1461
Thr Lys Met Ser Ser Met Asn Glu Arg Thr Ser Met Asn Glu Arg Glu
    355                 360                 365 acc ggc atg ctt tga tcctcactgt ggaacccctc aatggactct ctcaacccag     1516
Thr Gly Met Leu
370 ggacacccaa ggatatgtct tctgaagatc aaggcaagaa cctc                    1560

<210> SEQ ID NO 30
<211> LENGTH: 373
<212> TYPE: PRT
<213> ORGANISM: Homo sapiens

<400> SEQUENCE: 30

Met Arg Met Glu Asp Glu Asp Tyr Asn Thr Ser Ile Ser Tyr Gly Asp
1               5                   10                  15

Glu Tyr Pro Asp Tyr Leu Asp Ser Ile Val Val Leu Glu Asp Leu Ser
            20                  25                  30

Pro Leu Glu Ala Arg Val Thr Arg Ile Phe Leu Val Val Val Tyr Ser
        35                  40                  45

Ile Val Cys Phe Leu Gly Ile Leu Gly Asn Gly Leu Val Ile Ile Ile
    50                  55                  60

Ala Thr Phe Lys Met Lys Lys Thr Val Asn Met Val Trp Phe Leu Asn
65                  70                  75                  80

Leu Ala Val Ala Asp Phe Leu Phe Asn Val Phe Leu Pro Ile His Ile
                85                  90                  95

Thr Tyr Ala Ala Met Asp Tyr His Trp Val Phe Gly Thr Ala Met Cys
            100                 105                 110
```

Lys Ile Ser Asn Phe Leu Leu Ile His Asn Met Phe Thr Ser Val Phe
            115                 120                 125

Leu Leu Thr Ile Ile Ser Ser Asp Arg Cys Ile Ser Val Leu Leu Pro
        130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
            180                 185                 190

Phe Ser Leu Ser Thr Pro Gly Ser Ser Trp Pro Thr His Ser Gln
        195                 200                 205

Met Asp Pro Val Gly Tyr Ser Arg His Met Val Thr Val Thr Arg
210                 215                 220

Phe Leu Cys Gly Phe Leu Val Pro Val Leu Ile Ile Thr Ala Cys Tyr
225                 230                 235                 240

Leu Thr Ile Val Cys Lys Leu His Arg Asn Arg Leu Ala Lys Thr Lys
                245                 250                 255

Lys Pro Phe Lys Ile Ile Val Thr Ile Ile Thr Phe Phe Leu Cys
        260                 265                 270

Trp Cys Pro Tyr His Thr Leu Asn Leu Leu Glu Leu His His Thr Ala
        275                 280                 285

Met Pro Gly Ser Val Phe Ser Leu Gly Leu Pro Leu Ala Thr Ala Leu
290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
            325                 330                 335

Ala Leu Ser Glu Asp Thr Gly His Ser Ser Tyr Pro Ser His Arg Ser
        340                 345                 350

Phe Thr Lys Met Ser Ser Met Asn Glu Arg Thr Ser Met Asn Glu Arg
            355                 360                 365

Glu Thr Gly Met Leu
        370

<210> SEQ ID NO 31
<211> LENGTH: 23
<212> TYPE: RNA
<213> ORGANISM: Homo sapiens

<400> SEQUENCE: 31
ugagugugug ugugugagug ugu                                       23

<210> SEQ ID NO 32
<211> LENGTH: 22
<212> TYPE: RNA
<213> ORGANISM: Homo sapiens

<400> SEQUENCE: 32
aggcggggcg ccgcgggacc gc                                        22

<210> SEQ ID NO 33
<211> LENGTH: 21
<212> TYPE: RNA
<213> ORGANISM: Homo sapiens

<400> SEQUENCE: 33
agggagggac gggggcugug c                                              21

<210> SEQ ID NO 34
<211> LENGTH: 19
<212> TYPE: RNA
<213> ORGANISM: Homo sapiens

<400> SEQUENCE: 34
gagccaguug gacaggagc                                                 19

<210> SEQ ID NO 35
<211> LENGTH: 25
<212> TYPE: RNA
<213> ORGANISM: Homo sapiens

<400> SEQUENCE: 35
agggaucgcg ggcggguggc ggccu                                          25

<210> SEQ ID NO 36
<211> LENGTH: 23
<212> TYPE: RNA
<213> ORGANISM: Homo sapiens

<400> SEQUENCE: 36
aacauucauu gcugucggug ggu                                            23

<210> SEQ ID NO 37
<211> LENGTH: 22
<212> TYPE: RNA
<213> ORGANISM: Homo sapiens

<400> SEQUENCE: 37
ugagguagua guuuguacag uu                                             22

<210> SEQ ID NO 38
<211> LENGTH: 22
<212> TYPE: RNA
<213> ORGANISM: Homo sapiens

<400> SEQUENCE: 38
uguaaacauc cucgacugga ag                                             22

<210> SEQ ID NO 39
<211> LENGTH: 22
<212> TYPE: RNA
<213> ORGANISM: Homo sapiens

<400> SEQUENCE: 39
ucagugcacu acagaacuuu gu                                             22

<210> SEQ ID NO 40
<211> LENGTH: 22
<212> TYPE: RNA
<213> ORGANISM: Homo sapiens

<400> SEQUENCE: 40
auaaagcuag auaaccgaaa gu                                             22